United States Patent
Hook et al.

(10) Patent No.: US 9,802,887 B2
(45) Date of Patent: Oct. 31, 2017

(54) PROCESS FOR THE PREPARATION OF INTERMEDIATES USEFUL FOR THE MANUFACTURE NEP INHIBITORS

(71) Applicants: David Hook, Rheinfelden (CH); Bernhard Riss, Huningue (FR); Jianguang Zhou, Suzhou (CN); Yunzhong Li, Juangsu (CN); Erhard Bappert, Weil am Rhein (DE)

(72) Inventors: David Hook, Rheinfelden (CH); Bernhard Riss, Huningue (FR); Jianguang Zhou, Suzhou (CN); Yunzhong Li, Juangsu (CN); Erhard Bappert, Weil am Rhein (DE)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 14/739,197

(22) Filed: Jun. 15, 2015

(65) Prior Publication Data

US 2015/0274650 A1    Oct. 1, 2015

Related U.S. Application Data

(62) Division of application No. 13/818,576, filed as application No. PCT/EP2011/064411 on Aug. 22, 2011, now Pat. No. 9,085,529.

(30) Foreign Application Priority Data

Aug. 23, 2010 (WO) ................ PCT/CN2010/076249

(51) Int. Cl.
| | |
|---|---|
| C07C 229/34 | (2006.01) |
| C07C 271/22 | (2006.01) |
| C07C 227/22 | (2006.01) |
| C07C 227/20 | (2006.01) |
| C07C 269/06 | (2006.01) |
| C07D 207/267 | (2006.01) |
| C07D 207/27 | (2006.01) |
| C07D 207/33 | (2006.01) |
| C07D 207/38 | (2006.01) |
| C07C 227/18 | (2006.01) |
| C07D 207/24 | (2006.01) |
| C07D 207/277 | (2006.01) |
| C07C 229/30 | (2006.01) |
| C07C 231/10 | (2006.01) |

(52) U.S. Cl.
CPC .......... *C07C 271/22* (2013.01); *C07C 227/18* (2013.01); *C07C 227/20* (2013.01); *C07C 227/22* (2013.01); *C07C 229/30* (2013.01); *C07C 229/34* (2013.01); *C07C 231/10* (2013.01); *C07C 269/06* (2013.01); *C07D 207/24* (2013.01); *C07D 207/267* (2013.01); *C07D 207/27* (2013.01); *C07D 207/277* (2013.01); *C07D 207/33* (2013.01); *C07D 207/38* (2013.01); *C07B 2200/07* (2013.01)

(58) Field of Classification Search
CPC .................................................. C07C 229/34
See application file for complete search history.

(56) References Cited

U.S. PATENT DOCUMENTS 5,217,996 A    6/1993    Ksander

FOREIGN PATENT DOCUMENTS

| EP | 1903027 A1 | 3/2008 |
|---|---|---|
| WO | 2008083967 A2 | 7/2008 |
| WO | 2008138561 A1 | 11/2008 |
| WO | 2009090251 A2 | 7/2009 |

OTHER PUBLICATIONS

Trost (Comprehensive Organic Synthesis, (1991) vol. 1, part 1, p. 755-69 provided).*
Ksander, G M Et al: "Dicarboxylic Acid Dipeptide Neutral Endopeptidase Inhibitors", Journal of Medicinal Chemistry, American Chemical Society, vol. 38, No. 10, pp. 1689-1700.
Romano Di Fabio et al., Novel Stereocontrolled Addition of Allylmental Reagents to r-Imino Ester: Efficient Synthesis of Chiral Tetrahydroquinoline Derivatives, 2002, J. Org. Chem. vol. 67, p. 7319-7328.
Makoto Oba et al., Convenient synthesis of deuterated glutamic acid, proline and leucine via catalytic deuteration of unsaturated pyroglutamate derivatives, 2006, J Label Compd Radiopharm, vol. 49, p. 229-235.

* cited by examiner

*Primary Examiner* — Robert Havlin
(74) *Attorney, Agent, or Firm* — David R. Kurlandsky

(57) ABSTRACT

The invention relates to a new process for producing useful intermediates for the manufacture of NEP inhibitors or prodrugs thereof, in particular NEP inhibitors comprising a γ-amino-δ-biphenyl-α-methylalkanoic acid, or acid ester, backbone, such as N-(3-carboxyl-1-oxopropyl)-(4S)-(p-phenylphenylmethyl)-4-amino-(2R)-methyl butanoic acid ethyl ester or salt thereof.

3 Claims, 1 Drawing Sheet

(R)-5-Biphenyl-4-ylmethyl-3-methyl-2-oxo-2,5-dihydro-pyrrole-1-carboxylic acid tert-butyl ester (4a, R1 = Boc)
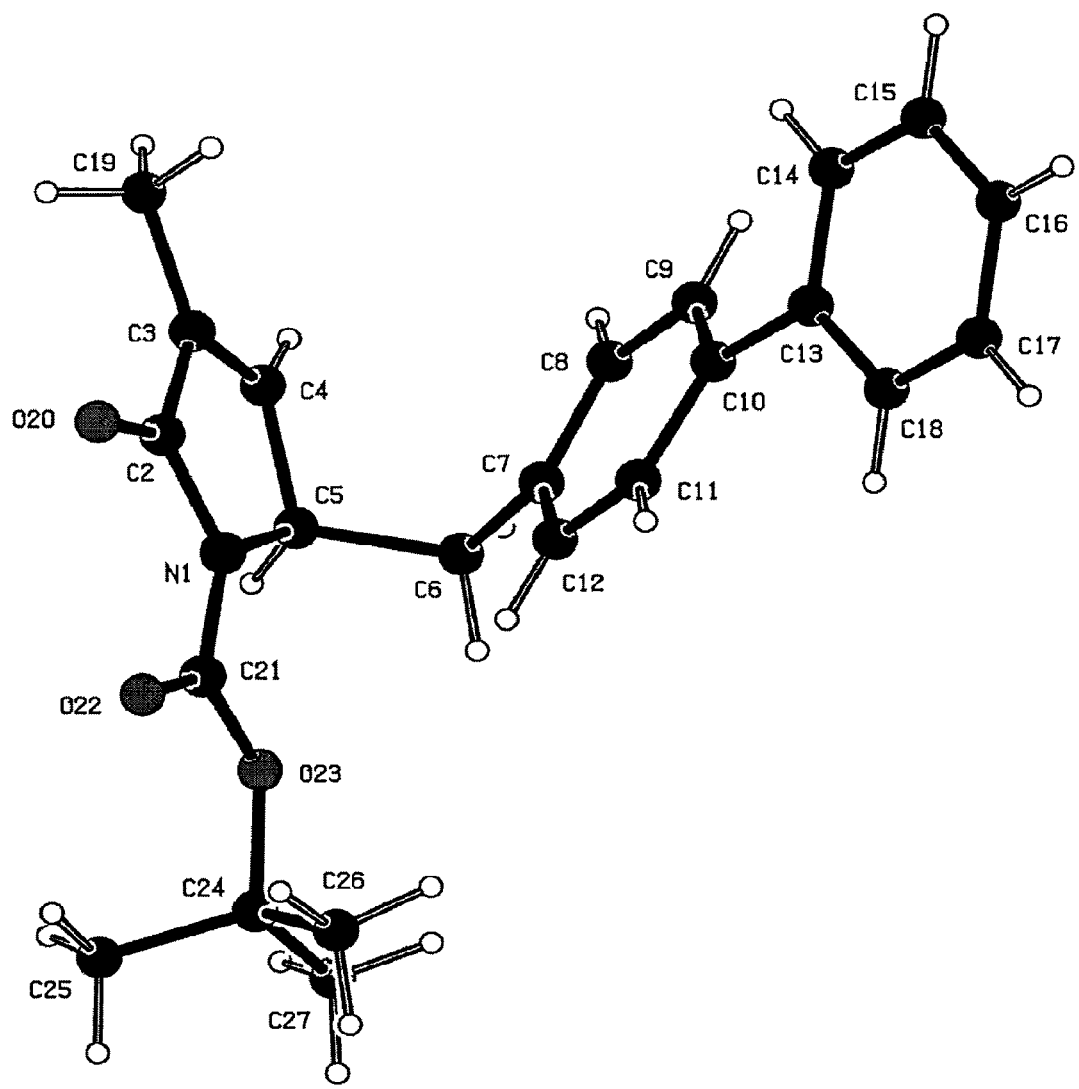

PROCESS FOR THE PREPARATION OF INTERMEDIATES USEFUL FOR THE MANUFACTURE NEP INHIBITORS

The invention relates to a new process for producing useful intermediates for the manufacture of NEP inhibitors or prodrugs thereof, in particular NEP inhibitors comprising a γ-amino-δ-biphenyl-α-methylalkanoic acid, or acid ester, backbone.

Endogenous atrial natriuretic peptides (ANP), also called atrial natriuretic factors (ANF) have diuretic, natriuretic and vasorelaxant functions in mammals. The natural ANF peptides are metabolically inactivated, in particular by a degrading enzyme which has been recognized to correspond to the enzyme neutral endopeptidase (NEP, EC 3.4.24.11), also responsible for e.g. the metabolic inactivation of enkephalins.

In the art biaryl substituted phosphonic acid derivatives are known which are useful as neutral endopeptidase (NEP) inhibitors, e.g. as inhibitors of the ANF-degrading enzyme in mammals, so as to prolong and potentiate the diuretic, natriuretic and vasodilator properties of ANF in mammals by inhibiting the degradation thereof to less active metabolites. NEP inhibitors are thus particularly useful for the treatment of conditions and disorders responsive to the inhibition of neutral endopeptidase (EC 3.4.24.11), particularly cardiovascular disorders such as hypertension, renal insufficiency including edema and salt retention, pulmonary edema and congestive heart failure.

Processes for preparing NEP-inhibitors are known. U.S. Pat. No. 5,217,996 describes biaryl substituted 4-aminobutyric acid amide derivatives which are useful as neutral endopeptidase (NEP) inhibitors, e.g. as inhibitors of the ANF-degrading enzyme in mammals. U.S. Pat. No. 5,217,996 discloses the preparation of N-(3-carboxyl-1-oxopropyl)-(4S)-(p-phenylphenylmethyl)-4-amino-(2R)-methyl butanoic acid ethyl ester. In the preparation of said compound N-t-butoxycarbonyl-(4R)-(p-phenylphenylmethyl)-4-amino-2-methyl-2-butenoic acid ethyl ester is hydrogenated in the presence of palladium on charcoal. WO2009/090251 relates to a reaction route for preparing compound N-t-butoxycarbonyl(4S)-(p-phenylphenylmethyl)-4-amino-2-methylbutanoic acid ethyl ester, or salt thereof, wherein an alternative hydrogenation step provides improved diastereoselectivity compared to that obtained in U.S. Pat. No. 5,217,996. A key intermediate of the route described in WO2009/090251 is a compound of formula (1),

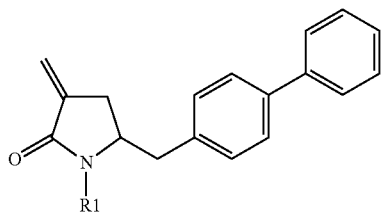

(1)

or salt thereof,
wherein R1 is hydrogen or a nitrogen protecting group.

According to WO2009/090251, a compound of formula (1) can be converted into a compound of formula (2), or salt thereof,

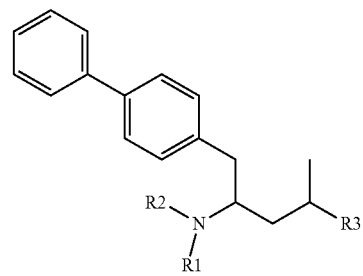

(2)

wherein R1 and R2 are, independently of each other, hydrogen or a nitrogen protecting group, and R3 is a carboxyl group or an ester group, preferably carboxyl group or alkyl ester. Compounds of formula (2) can be used as intermediates in the preparation of NEP inhibitors, or prodrugs thereof, in particular NEP inhibitors comprising a γ-amino-δ-biphenyl-α-methylalkanoic acid, or acid ester, backbone, preferably N-(3-carboxyl-1-oxopropyl)-(4S)-(p-phenylphenylmethyl)-4-amino-(2R)-methyl butanoic acid ethyl ester, for example, as described in the Journal of Medicinal Chemistry, 1995, 38, 1689.

Alternatively, a compound of formula (2), as described above, can be prepared from a compound of formula (3)

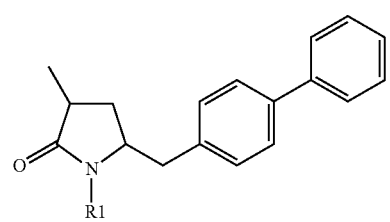

(3)

or salt thereof,
wherein R1 is hydrogen or a nitrogen protecting group,
as described in WO2008/083967.

The object of the present invention is to provide an alternative process for preparing NEP inhibitors or prodrugs thereof starting from a compound of formula (1) or (3), as described herein. In particular, the provision of alternative processes for producing a compound of formula (2), as described herein, by starting from either a compound of formula (1) or (3), as described herein, is an object of the present invention. The development of alternative routes to intermediates useful in the synthesis of pharmaceutical products provides means to find methods which are, for example, advantageous in an economic sense, from the technical point of view, or otherwise, in particular for large scale manufacture. Moreover, the discovery of new intermediates useful in the synthesis of pharmaceutical products opens the way to new chemical processes for preparing known end products and they thus enrich the chemical ground.

The new processes, according to the present invention, for producing a compound according to formula (2), or salt thereof, as defined herein, are summarized in Schemes 1, 2 and 3.

Scheme 1

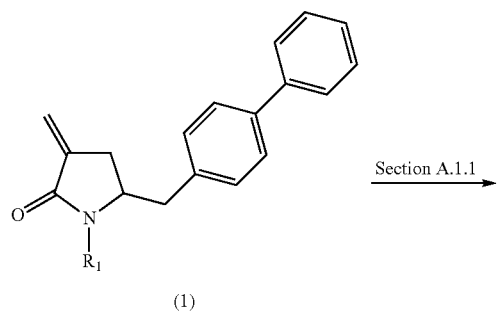

(1) →[Section A.1.1]

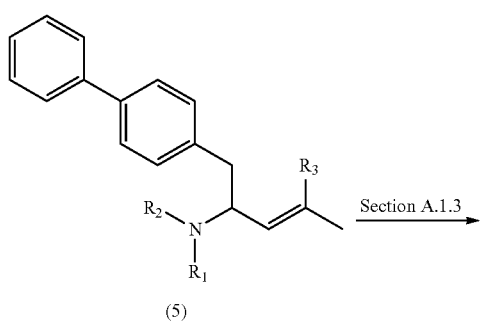

(4) ↓[Section A.1.2]

(5) →[Section A.1.3]

(2)

Scheme 2

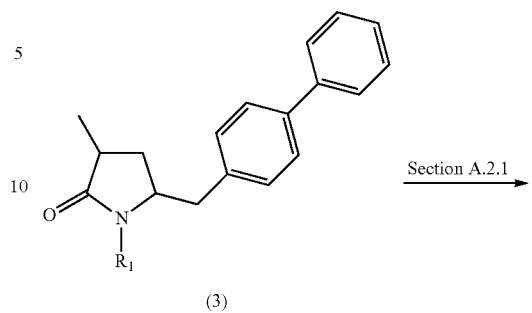

(3) →[Section A.2.1]

(4) ↓[Section A.1.2]

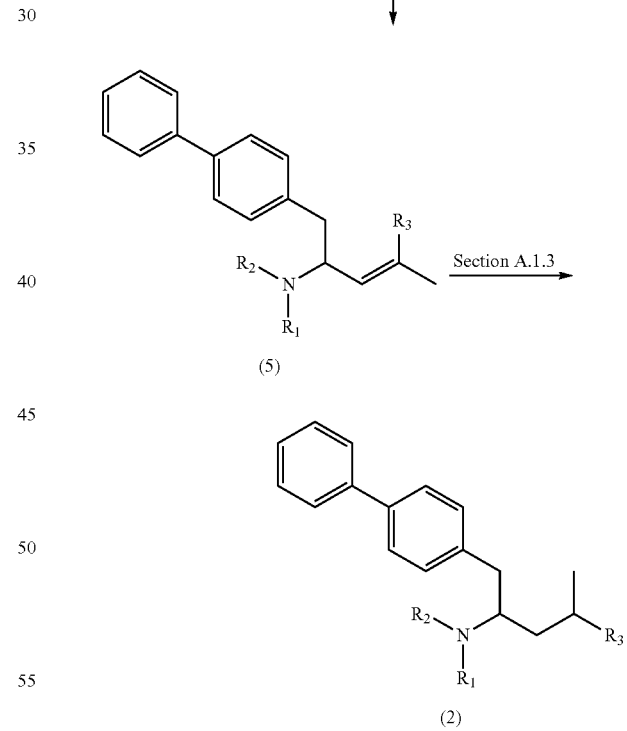

(5) →[Section A.1.3]

(2)

As shown in Scheme 1, a compound of formula (1), as described herein, is converted into a compound of formula (2), or salt thereof, wherein R1 is hydrogen or a nitrogen protecting group, according to the method described in Section A.1, which comprises steps described in Sections A.1.1, A1.2 and A.1.3.

As shown in Scheme 2, a compound of formula (3), as described herein, is converted into a compound of formula (2), or salt thereof, wherein R1 is hydrogen or a nitrogen protecting group, according to the method described in Section A.2, which comprises the steps described in Sections A.2.1, A.1.2 and A.1.3.

Scheme 3

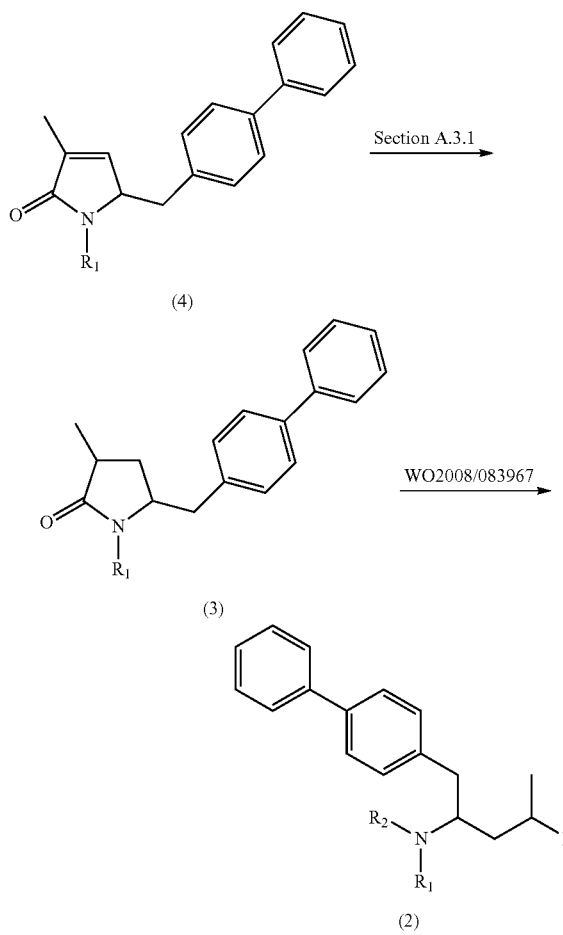

As shown in Scheme 3, a compound of formula (4), as described herein, is converted into a compound of formula (2), or salt thereof, wherein R1 is hydrogen or a nitrogen protecting group, according to the method described in Section A.3, which comprises the step described in Section A.3.1.

The invention as a whole comprises the following sections:
Section A: Preparation methods for the compound of formula (2)
Section B: Novel and inventive compounds
Section C: Examples It is noted that in the present application usually explanations made in one section are also applicable for other sections, unless otherwise stated. When referring to compounds described in the present invention, it is understood that reference is also being made to salts thereof. Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms.

In a further embodiment, the present invention also relates to a process for preparing N-(3-carboxyl-1-oxopropyl)-(4S)-(p-phenylphenylmethyl)-4-amino-(2R)-methyl butanoic acid ethyl ester, or a salt thereof, comprising the manufacture of compound of formula (2), or salt thereof, as defined above, according to the methods described herein.

FIG. 1: X-ray Structure of (R)-5-Biphenyl-4-ylmethyl-3-methyl-2-oxo-2,5-dihydro-pyrrole-1-carboxylic acid tert-butyl ester (4a, R1=Boc) crystals

SECTION A: PREPARATION OF A COMPOUND OF FORMULA (2)

Section A.1:

In a first aspect, the invention relates to a process to convert a compound of formula (1), or salt thereof, as defined herein, into a compound of formula (2), or salt thereof, as defined herein, as outlined in Scheme 1 above, wherein compounds of formula (4) and (5) are as defined herein. Intermediate process steps described in sections A.1.1, A.1.2 and A.1.3 are also embodiments of the present invention.

Section A.1.1: Synthesis of a Compound of Formula (4)

In one embodiment, the present invention relates to a process for preparing a compound of formula (4), or salt thereof,

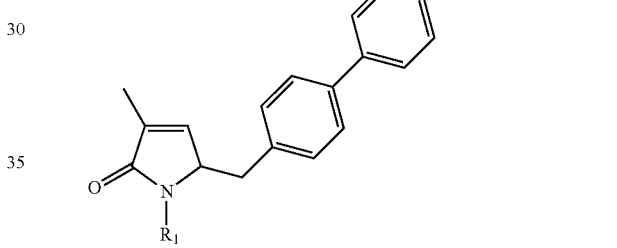

wherein
R1 is hydrogen or a nitrogen protecting group;
said process comprising
reacting a compound of formula (1), or salt thereof,

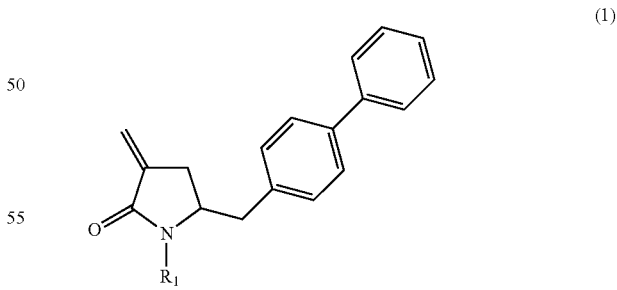

wherein R1 is hydrogen or a nitrogen protecting group;
with a transition metal catalyst, optionally in the presence of a base,
to obtain the compound of formula (4), or salt thereof.

In a preferred embodiment, the present invention relates to a process for preparing a compound of formula (4a), or salt thereof,

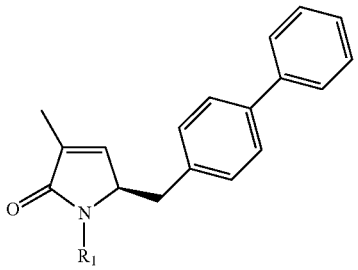

(4a)

wherein
R1 is hydrogen or a nitrogen protecting group;
said process comprising
reacting a compound of formula (1a), or salt thereof,

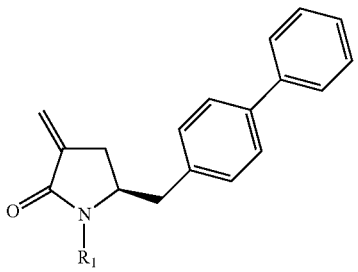

(1a)

wherein R1 is hydrogen or a nitrogen protecting group;
with a transition metal catalyst, optionally in the presence of a base, to obtain the compound of formula (4a), or salt thereof.

Suitable transition metal catalysts for the conversion of a compound of formula (1), preferably of formula (1a), as described herein, into a compound of formula (4), preferably of formula (4a), as described herein, include, for example, catalysts wherein the transition metal is selected from group 8, 9 or 10 of the periodic table. Therefore, the transition metal catalyst comprises, for example Ruthenium (Ru), Rhodium (Rh), Palladium (Pd) or Platinum (Pt), preferably the transition metal catalyst comprises palladium, such as Pd/C or Pd(Ph$_3$)$_4$. Further suitable transition metal catalysts are, for example, those described in Sections B.3.3, C.2 or D.4 in WO2009/090251, which are incorporated by reference herein.

Suitable bases are, for example, an amine {eg diphenylamine, diisopropylamine, dimethylamine or imidazole, triethylamine, pyridine, 1,8-diazabicyclo[5.4.0]undec-7-ene (DBU), iPr$_2$EtN or 1,4-diazabicyclo[2.2.2]octane}, an alkali metal carbonate (eg sodium carbonate, potassium carbonate or cesium carbonate), an alkali earth metal carbonate (eg calcium carbonate, barium carbonate), an alkali metal hydrogen carbonate (eg NaHCO$_3$), an alkali metal hydroxide (eg sodium hydroxide, lithium hydroxide) or an alkali metal hydroxide (eg calcium hydroxide).

Section A.1.2: Ring Opening of a Compound of Formula (4)

In another aspect, the present invention relates to a process for preparing a compound according to formula (5),

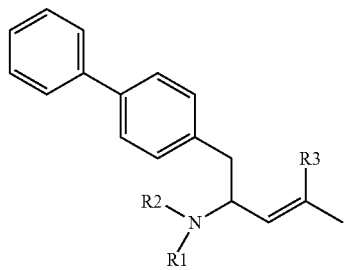

(5)

or salt thereof,
wherein R1 and R2 are, independently of each other, hydrogen or a nitrogen protecting group, and R3 is a carboxyl group or an ester group, preferably a carboxyl group, comprising reacting a compound of formula (4)

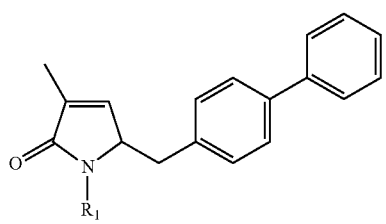

(4)

or salt thereof,
wherein R1 is hydrogen or a nitrogen protecting group, with a lactam ring opening agent to obtain the compound of formula (5).

In a preferred embodiment, a compound of formula (4a)

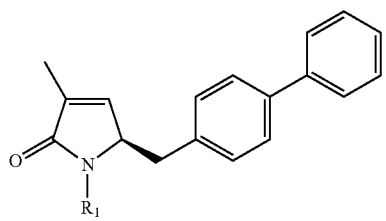

(4a)

or salt thereof,
wherein R1 is hydrogen or a nitrogen protecting group, is treated with a lactam ring opening agent to obtain a compound according to formula (5a),

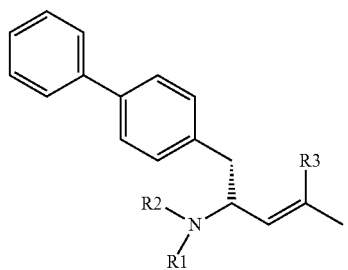

(5a)

or salt thereof, wherein R1 and R2 are, independently of each other, hydrogen or a nitrogen protecting group, and R3 is a carboxyl group or an ester group, preferably a carboxyl group.

Examples of lactam ring opening agents are nucleophilic bases such as alkali metal hydroxides (for example sodium hydroxide or lithium hydroxide) or alkali metal alkoxides (for example sodium alkoxide or lithium alkoxide, such a sodium ethoxide or lithium ethoxide), neutral compounds such as hydrogenperoxides (such as lithium hydrogenperoxide) and acids. Acids are, for example, Lewis or Brønsted acids, mineral acids such as sulphuric, perchloric and hydrochloric acid, sulphonic acids such as para-toluenesulphonic acid or polymer-bound acids such as Amberlyst®. Acids may be used in the presence of water or an alcohol (such as methanol or ethanol). The lactam ring opening agent can be used catalytically or stoichiometrically. Preferably, the lactam ring opening agent is an alkali metal hydroxide, for example lithium hydroxide.

Section A.1.3: Reduction of a Compound of Formula (5)

In another embodiment, the subject-matter of the present invention relates to a process for preparing a compound according to formula (2),

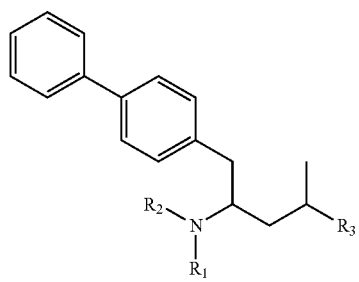

(2)

or salt thereof, wherein R1 and R2 are, independently of each other, hydrogen or a nitrogen protecting group, and R3 is a carboxyl group or an ester group, preferably a carboxyl group, comprising reducing a compound according to formula (5),

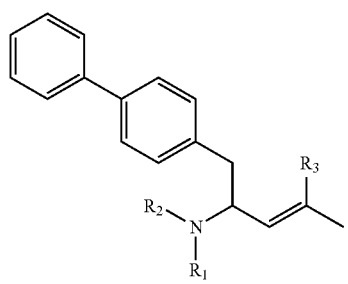

(5)

or salt thereof, wherein R1 and R2 are, independently of each other, hydrogen or a nitrogen protecting group, and R3 is a carboxyl group or an ester group, preferably a carboxyl group, to obtain the compound of formula (2).

Preferably, a compound according to formula (5a), or salt thereof,

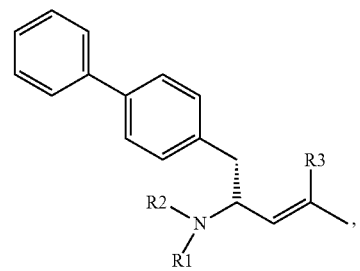

(5a)

wherein R1, R2 and R3 are defined as above, is used as starting compound. If the compound (5a), or salt thereof, is used as starting compound, compounds according to formula (2a)

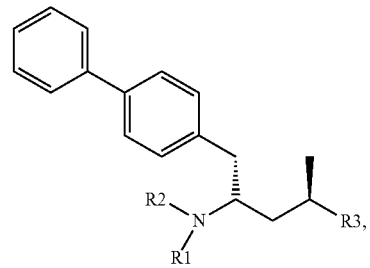

(2a)

and formula (2b),

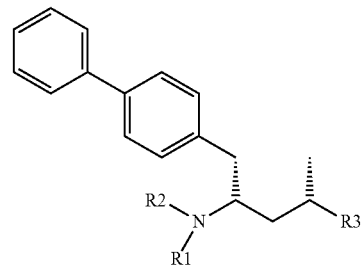

(2b)

or salts thereof, wherein R1, R2 and R3 are defined as above, can be obtained.

In a preferred embodiment, the present invention relates to a process for preparing a compound according to formula (2a),

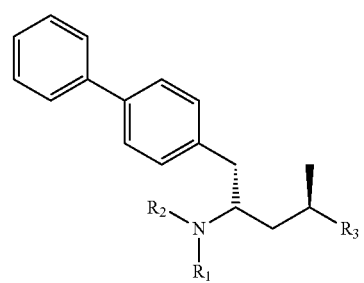

(2a)

or salt thereof,
wherein R1 and R2 are, independently of each other, hydrogen or a nitrogen protecting group, and R3 is a carboxyl group or an ester group, preferably a carboxyl group, comprising reducing a compound according to formula (5a),

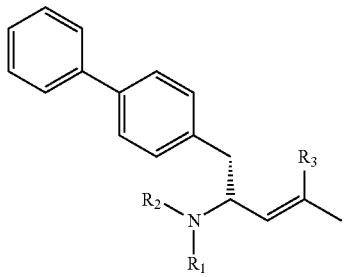

or salt thereof,
wherein R1 and R2 are, independently of each other, hydrogen or a nitrogen protecting group, and R3 is a carboxyl group or an ester group, preferably a carboxyl group, to obtain the compound of formula (2a).

Preferably, the reduction of the compound of formula (5), or salt thereof, preferably of formula (5a), takes place with hydrogen in the presence of a transition metal catalyst. The transition metal catalyst comprises an organometallic complex and a chiral ligand or is an organometallic catalyst.

The reduction may occur under heterero- or homogeneous hydrogenation conditions, preferably under heterogeneous hydrogenation conditions.

Generally, the heterogeneous hydrogenation is carried out in the presence of a transition metal catalyst on a solid support, wherein the transition metal is selected from group 9 or 10 of the periodic table. Therefore, the transition metal catalyst comprises, for example, Cobalt (Co), Rhodium (Rh), Iridium (Ir), Nickel (Ni), Palladium (Pd) and/or Platinum (Pt). Solid supports are, for example, carbon, metal oxides (e.g. aluminium oxide, zirconium oxide, titanium oxide or silicon dioxide/aluminium oxide), sulfates (e.g. barium sulfate) or carbonates (e.g. calcium carbonate and barium carbonate). The loading of the transition metal on the solid support is, for example, of from 1% to 10% w/w. In one embodiment, the transition metal catalyst may contain water, for example, of from 0 mass % to 50 mass % content of water. In particular, the transition metal catalyst is Pt, Pd, or Rh on a solid support, such as carbon. In one embodiment the transition metal catalyst is Pd on carbon.

The heterogeneous hydrogenation is usually performed in a solvent, such as ether solvents (eg THF), ester solvents (eg isopropyl acetate) or alcohol solvents (eg isopropanol, ethanol or methanol); in particular isopropyl acetate and ethanol.

In one embodiment, under heterogeneous hydrogenation conditions, a suitable transition metal catalyst is, for example, Pd or Rh on carbon. Under this conditions, the reduction of the compound of formula (5a), or salt thereof, wherein R1 and R2 are defined as above, and R3 is $CO_2H$, provides a composition comprising the compounds according to formulae (2a) and (2b), or salts thereof, wherein the molar ratio of compounds according to formula (2a), or salts thereof, to compounds according to formula (2b), or salts thereof, is at least 51 to 49, such as 54 to 46.

In another embodiment, under heterogeneous hydrogenation conditions, a suitable transition metal catalyst is, for example, Pt on carbon. Under this conditions, the reduction of the compound of formula (5a), or salt thereof, wherein R1 and R2 are defined as above, and R3 is $CO_2H$, provides a composition comprising the compounds according to formulae (2a) and (2b), or salts thereof, wherein the molar ratio of compounds according to formula (2b), or salts thereof, to compounds according to formula (2a), or salts thereof, is at least 51 to 49, such as 58 to 42.

Generally, the homogeneous hydrogenation is carried out in the presence of a transition metal catalyst, wherein the transition metal is selected from group 7, 8 or 9 of the periodic table. Therefore, the transition metal catalyst comprises, for example, the transition metal Manganese (Mn), Rhenium (Re), Iron (Fe), Ruthenium (Ru), Osmium (Os), Cobalt (Co), Rhodium (Rh) and/or Iridium (Ir).

In a preferred embodiment, the transition metal catalyst comprises an organometallic complex and a chiral ligand or is an organometallic catalyst.

The organometallic complex comprises a transition metal selected from group 7, 8 or 9 of the periodic table, for example the transition metal rhodium, iridium or ruthenium in particular rhodium or ruthenium. An organometallic complex comprising rhodium is particularly suitable.

The organometallic complexes can comprise a single transition metal atom. In preferred embodiments the complexes can comprise two or more transition metal atoms, optionally comprising a metal-metal bond. In a preferred embodiment two metal atoms are bridged via two halides. Generally, the organometallic complex, comprises one or more transition metal atoms and suitable achiral ligands.

Suitable achiral ligands for the organometallic complex generally are σ-donor ligands, σ-donor/π-acceptor ligands or σ,π-donor/π-acceptor ligands. Examples for suitable achiral ligands are among others carbon monoxide, halides (e.g. Cl, I or Br), phosphines [e.g. tricyclohexylphosphine ($PCy_3$)], alkenyls (e.g. cyclooctadiene (cod), norbornadiene (nbd), 2-metallyl)], alkynyls, aryls (e.g. pyridine, benzene, p-cymene), carbonyls (e.g. acetylacetonate (acac), trifluoroacetate or dimethylformamide) and mixtures thereof.

Examples of preferred achiral ligands for the organometallic complex are: norbornadiene (nbd), cyclooctadiene (cod), pyridine (pyr), cymene, in particular p-cymene, and iodide.

Examples for organometallic complexes are: a ruthenium organometallic complex, such as $[RuI_2(\text{p-cymene})]_2$, $[RuCl_2(\text{p-cymene})]_2$, $[Ru(cod)(2\text{-metallyl})_2]$ or $[Ru(cod)(OOCCF_3)_2]$; a rhodium organometallic complex, such as $[Rh(nbd)_2]BF_4$, $[Rh(cod)_2]O_3SCF_3$ or $[Rh(cod)_2]BF_4$; or an iridium organometallic complex such as $[(Cy_3P)Ir(pyr)]Cl$, $[Ir(cod)_2]BArF$ or $[Ir(cod)_2Cl]_2$; in particular $[Rh(cod)_2]O_3SCF_3$, $[Rh(nbd)_2]BF_4$ or $[Ru(cod)(OOCCF_3)_2]$; preferably $[Rh(nbd)_2]BF_4$ or $[Rh(cod)_2]O_3SCF_3$.

In one embodiment the organometallic complex is [Rh(nbd)$_2$]BF$_4$ {=Bis(norbornadiene)rhodium(I) tetrafluoroborate}.

In another embodiment, the organometallic complex is $[RuI_2(\text{p-cymene})]_2$ (=Diiodo(p-cymene)ruthenium(II) dimer).

Generally, the term "chiral ligand" comprises any ligand that is suitable to build chiral organometallic complexes and that comprises a chiral centre. The transition metal catalyst comprises an organometallic complex and a chiral ligand. The chiral ligand comprises, for example, a chiral phosphine and/or a chiral ferrocene. In particular, the chiral ferrocene comprises a Cp (cyclopentadienyl) moiety which is substituted with a chiral group, such as a chiral amine, a chiral phosphine or a chiral alkyl, for example as illustrated herein.

Suitable chiral ligands are, for example, ligands described in WO2009/090251, in Section C.2 and in examples therein, and are incorporated herein by reference, in particular, phospholane ligands, BoPhoz ligands, BINAP ligands, BINOL ligands, P-Phos ligands, ProPhos ligands, BDPP ligands, DIOP ligands, DIPAMP ligands, DuanPhos ligands, NorPhos ligands, BINAM ligands, CatASium ligands, SimplePHOX ligands, PHOX ligands, ChiraPhos ligands, Ferrotane ligands, BPE ligands, TangPhos ligands, JafaPhos ligands, DuPhos ligands, Binaphane ligands, QuinaPhos ligands, Atropisomer ligands, Fenphos ligands, Josiphos ligands, Mandyphos ligands, Taniaphos ligands, Walphos ligands, PhanePhos, UbaPHOX, SpiroP or (R)-SDP ligand.

BINAP ligands are for example, as described in R. Noyori, H. Takaya, Acc. Chem. Res., 23 345 (1990), for example R is phenyl (=BINAP) or tolyl (=Tol-BINAP). In particular, suitable BINAP ligands are (R)-BINAP, (R)-Tol-BINAP, (S)-BINAP or (S)-Tol-BINAP.

(R)-2,2'-Bis(di-p-tolylphosphino)-1,1'-binapthalene=(R)-Tol-BINAP
(S)-2,2'-Bis(di-p-tolylphosphino)-1,1'-binapthalene=(S)-Tol-BINAP
(R)-2,2'-Bis(diphenylphosphino)-1,1'-binapthalene=(R)-BINAP
(S)-2,2'-Bis(diphenylphosphino)-1,1'-binapthalene=(S)-BINAP
(R)-(+)-2,2'-Bis[di(3,5-xylyl)phosphino]-1,1'-binaphthyl=(R)-Xyl-BINAP
(S)-(+)-2,2'-Bis[di(3,5-xylyl)phosphino]-1,1'-binaphthyl=(S)-Xyl-BINAP BDPP ligands are for example, as described in Bakos, J.; Toth, I.; Marko, L. J. Org. Chem., 46, 5427 (1981), for example R is Ph. In particular, suitable BDPP ligands are, for example, (R,R)-BDPP or (S,S)-BDPP.

(2R,4R)-2,4-Bis(diphenylphosphino)pentane=(R,R)-BDPP
(2S,4S)-2,4-Bis(diphenylphosphino)pentane=(S,S)-BDPP DIOP ligands are for example, as described in Kagan, H. B.; Dang, T. P. Chem. Commun. 1971, 481; Kagan, H. B.; Dang, T. P. J. Am. Chem. Soc., 94, 6429 (1972); Yan, Yuan-Yong; RajanBabu, T. V.; Organic Letters, 2000, 2(26), 4137; Brown, J. M.; Chaloner, P. A.; J. Chem. Soc., Chem. Commun., 1978, (7), 321, for example R is Ph or 4-methoxy-3,5-dimethylphenyl. In particular, suitable DIOP ligands are, for example:

(4R,5R)-4,5-Bis(diphenylphosphino-methyl)-2,2-dimethyl-1,3-dioxolane=(R,R)-DIOP
(4S,5S)-4,5-Bis(diphenylphosphino-methyl)-2,2-dimethyl-1,3-dioxolane=(S,S)-DIOP
(R)-(−)-5,5'-Bis[di(3,5-di-t-butyl-4-methoxyphenyl)phosphino]-4,4'-bi-1,3-benzodioxole=(R,R)-MOD-DIOP ChiraPhos ligands are for example, as described in Fryzuk, M. B.; Bosnich, B. J. Am. Chem. Soc, 99, 6262 (1977); Fryzuk, M. B.; Bosnich, B. J. Am. Chem. Soc, 101, 3043 (1979), for example R is Ph. In particular, a suitable ChiraPhos ligand is, for example, (S,S)-ChiraPhos.

(2S,3S)-(−)-Bis(diphenylphosphino)butane=(S,S)-Chiraphos
(2R,3R)-(+)-Bis(diphenylphosphino)butane=(R,R)-Chiraphos PhanePhos ligands are for example, as described in K. Rossen, P. J. Pye, R. A. Reamer, N. N. Tsou, R. P. Volante, P. J. Reider J. Am. Chem. Soc. 119, 6207 (1997), for example Ar is Ph (=PhanePhos), 4-Me-$C_6H_4$ (=Tol-PhanePhos), 4-MeO—$C_6H_4$ (=An-PhanePhos), 3,5-$Me_2$-$C_6H_3$ (=Xyl-Phanephos) or 3,5-$Me_e$-4-MeO-$C_6H_2$ (=MeO-Xyl-Phanephos). In particular, suitable PhanePhos ligands are, for example, (R)-PhanePhos, (R)-Xyl-PhanePhos, (S)-Xyl-PhanePhos, (S)-PhanePhos, (R)-An-PhanePhos, (R)-MeO-Xyl-PhanePhos or (R)-Tol-PhanePhos.

(R)-4,12-Bis(diphenylphosphino)-[2.2]-paracyclopentane=(R)-PhanePhos
(S)-4,12-Bis(diphenylphosphino)-[2.2]-paracyclopentane=(S)-PhanePhos
(R)-4,12-Bis(di(3,5-xylyl)phosphino)-[2.2]-paracyclopentane=(R)-Xyl-PhanePhos
(S)-4,12-Bis(di(3,5-xylyl)phosphino)[2.2]-paracyclopentane=(S)-Xyl-PhanePhos
(R)-4,12-Bis(di(p-tolyl)phosphino)[2.2]-paracyclopentane=(R)-Tol-PhanePhos
(R)-4,12-Bis(di(p-methoxyphenyl)phosphino)-[2.2]-paracyclopentane=(R)-An-PhanePhos
(R)-4,12-Bis(di(p-methoxy-3,5-dimethylphenyl)phosphino)[2.2]-paracyclopentane=(R)-MeO-Xyl-PhanePhos Mandyphos ligands are for example:
(αS,αS)-2,2'-bis(α-N,N-dimethylaminophenylmethyl)-(R,R)-1,1'-bis(dicyclohexylphosphino)ferrocene (=Mandyphos SL-M002-2)
(αR,αR)-2,2'-Bis(α-N,N-dimethylaminophenylmethyl)-(S,S)-1,1'-bis(diphenylphosphino)ferrocene (=Mandyphos SL-M001-1)
(αR,αR)-2,2'-bis(α-N,N-dimethylaminophenylmethyl)-(S,S)-1,1'-bis(dicyclohexylphosphino)ferrocene (=Mandyphos SL-M002-1)
(αR,αR)-2,2'-Bis(α-N,N-dimethylaminophenylmethyl)-(S,S)-1,1'-bis-[di(bis-(3,5-trifluoromethyl)phenyl)-phosphino]ferrocene (=Mandyphos SL-M003-1)
(αR,αR)-2,2'-Bis(α-N,N-dimethylaminophenylmethyl)-(S,S)-1,1'-bis[di(3,5-dimethyl-4-methoxyphenyl)phosphino]ferrocene (=Mandyphos SL-M004-1)
(αS,αS)-2,2'-Bis(α-N,N-dimethylaminophenylmethyl)-(R,R)-1,1'-bis[di(3,5-dimethyl-4-methoxyphenyl)phosphino]ferrocene (=Mandyphos SL-M004-2)
(αR,αR)-2,2'-Bis(α-N,N-dimethylaminophenylmethyl)-(S,S)-1,1'-bis[di(3,5-dimethylphenyl)phosphino]ferrocene (=Mandyphos SL-M009-1)
(1R,1'R)-1,1'-Bis[bis(3,5-tert-butyl-4-methoxyphenyl)phosphino]-2,2'-bis[(R)-(dimethylamino)phenylmethyl]ferrocene (=Mandyphos SL-M010-1)
(αR,αR)-2,2'-Bis(α-N,N-dimethytaminophenylmethyl)-(S,S)-1,1'-bis[di-(2-methylphenyl)phosphino]-ferrocene (=Mandyphos SL-M012-1)

Josiphos ligands are for example:
(R)-1-[(S)-2-(Bis(2-napthyl)-phosphino)ferrocenyl]ethyldi-tert.-butylphosphine (=Josiphos SL-J216-1)
(S)-1-[(R)-2-Bis(2-isopropoxyphenyl)phosphino)ferrocenyl]ethyldi-tert-butylphosphine (=Josiphos SL-J226-2)
(S)-1-[(R)-2-Diphenylphosphino)ferrocenyl]ethyldi-tert.-butylphosphine (=Josiphos SL-J002-2)
(R)-1-[(S)-2-cyclohexylphosphino)ferrocenyl]ethyl diphenylphosphine (=Josiphos SL-J004-1)
(S)-1-[(R)-2-Di(4-trifluoromethylphenyl)phosphino)ferrocenyl]ethyldi-tert.-butylphosphine (=Josiphos SL-J011-2)
(R)-1-[(S)-2-[Bis(4-methyl-phenyl)phosphino]ferrocenyl}ethyldi-tert.-butylphosphine (=Josiphos SL-J012-1)
(S)-1-[($R_P$)-2-[Bis(4-methoxy-3,5-dimethyl-phenyl)phosphino]ferrocenyl}ethyldi-tert.-butylphosphine (=Josiphos SL-J013-2)
(R)-1-[(S)-2-[Bis(4-fluoro-phenyl)phosphino]ferrocenyl}ethyldi-tert-butylphosphine (=Josiphos SL-J014-1)
(R)-1-[(S)-2-[Bis(4-methoxy-phenyl)phosphino]ferrocenyl}ethyldi-tert.-butylphosphine (=Josiphos SL-J202-1)

(S)-1-[(R)-2-(Bis(2-furyl)-phosphino)ferrocenyl]ethyldi-tert-butylphosphine (=Josiphos SL-J212-2)
(S)-1-[(R)-2-(Bis(2-napthyl)-phosphino)ferrocenyl]ditert.-butylphosphine (=Josiphos SL-J216-2)
(S)-1-[(R)-2-diethylphosphino)ferrocenyl]ethyl di(tert-butyl)-phosphine (=Josiphos SL-J301-2)
(S)-1-[(R)-2-di(tert-butyl)-phosphino)ferrocenyl]ethyl diphenylphosphine (=Josiphos SL-J502-2)
1-[(1,1-dimethylethyl)phosphinyl]-2-[(1R)-1-(diphenylphosphino)ethyl]-(1R)-ferrocene (=Josiphos SL-J681-1)
1-[(1,1-dimethylethyl)phosphinyl]-2-[(1S)-1-(diphenylphosphino)ethyl]-(1S)-ferrocene (=Josiphos SL-J681-2)
(S)-1-[(R)-2-[Bis(4-fluorophenyl)phosphino]ferrocenyl}ethyldi-tert-butylphosphine (=Josiphos SL-J014-2)
(R)-1-[(S)-2-(Di-2-furylphosphino)-ferrocenyl]ethyldi-3,5-xylylphosphine (=Josiphos SL-J015-1)
(R)-1-[(S)-2-Di-(3,5-bis(trifluoromethyl)phenyl)phosphino)ferrocenyl]ethyldi-t-butylphosphine Josiphos SL-J210-1)
(S)-1-[(R)-2-Di-2-furylphosphino)ferrocenyl]ethyldi-(2-methylphenyl)phosphine (=Josiphos SL-J452-2)
(S)-1-[(R)-2-Di-(3,5-bis(trifluoromethyl)phenyl)phosphino)ferrocenyl]ethyldi-t-butylphosphine (=Josiphos SL-J210-2)
(R)-1-[(S)-2-Diphenylphosphino)ferrocenyl]ethyldi-tert.-butylphosphine (=Josiphos SL-J002-1)
(R)-1-[(S)-2-Dicyclohexylphosphino)ferrocenyl]ethyldicyclohexylphosphine (=Josiphos SL-J003-1)
(R)-1-[(S)-2-(Diphenylphosphino)ferrocenyl]ethyldi(3,5-xylyl)phosphine (=Josiphos SL-J005-1)
(S)-1-[(R)-2-(Diphenylphosphino)ferrocenyl]ethyldi(3,5-xylyl)phosphine (=Josiphos SL-J005-2)
(R)-1-[(S)-2-Di-(3,5-bis(trifluoromethyl)phenyl)-phosphino)ferrocenyl]ethyldicyclohexylphosphine (=Josiphos SL-J006-1)
(S)-1-[(S)-2-Di-(3,5-bis(trifluoromethyl)phenyl)-phosphino)ferrocenyl]ethyldicyclohexylphosphine Josiphos SL-J006-2)
(R)-1-[(S)-2-Di-(3,5-bis(trifluoromethyl)phenyl)-phosphino)-ferrocenyl]ethyldi(3,5-dimethylphenyl)phosphine (=Josiphos SL-J008-1)
(R)-1-[(S)-2-Dicyclohexylphosphino)ferrocenyl]ethyldi-tert-butylphosphine (=Josiphos SL-J009-1)
(R)-1-[(S)-2-Di(4-trifluoromethylphenyl)phosphino)ferrocenyl]ethyldi-tert.-butylphosphine (=Josiphos SL-J011-1)
(R)-1-[(S$_P$)-2-[Bis(4-methoxy-3,5-dimethylphenyl)phosphino]ferrocenyl}ethyldi-tert-butylphosphine (=Josiphos SL-J013-1)
(R)-1-[(S)-2-bis(2-methylphenyl)phosphino)ferrocenyl]ethyl di(tert-butyl)phosphine (=Josiphos SL-J211-1)
(R)-1-[(S)-2-diethylphosphino)ferrocenyl]ethyl di(tert-butyl)-phosphine (=Josiphos SL-J301-1)
(R)-1-[(S)-2-Di-ethylphosphino)ferrocenyl]ethyldi-(2-methylphenyl)phosphine (=Josiphos SL-J302-1)
(R)-1-[(S)-2-bis(4-trifluoromethylphenyl)phosphino)ferrocenyl]ethyl bis(4-trifluoromethyl)-phosphine (=Josiphos SL-J403-1)
(R)-1-[(S)-2-bis(3,5-dimethylphenyl)phosphino)ferrocenyl]ethyl bis(3,5-dimethylphenyl)-phosphine (=Josiphos SL-J408-1)
(R)-1-[(S)-2-bis(3,5-dimethylphenyl)phosphino)ferrocenyl]ethyl bis[bis-(3,5-trifluoro-methyl)phenyl]-phosphine (=Josiphos SL-J412-1)
(R)-1-[(S)-2-bis(2-methoxyphenyl)phosphino)ferrocenyl]ethyl bis(2-methoxyphenyl)-phosphine (=Josiphos SL-J430-1)
(R)-1-[(S)-2-bis(2-isopropoxyphenyl)phosphino)ferrocenyl]ethyl bis(3,5-dimethylphenyl)-phosphine (=Josiphos SL-J431-1)
(R)-1-[(S)-2-di(tert-butyl)phosphino)ferrocenyl]ethyl bis(3,5-dimethylphenyl)-phosphine (=Josiphos SL-J501-1)
(R)-1-[(S)-2-diethylphosphino)ferrocenyl]ethyl bis(2-methylphenyl)-phosphine (=Josiphos SL-J503-1)
(R)-1-[(S)-2-cyclohexylphosphino)ferrocenyl]ethyl bis(2-methylphenyl)-phosphine (=Josiphos SL-J504-1)
(S)-1-[(R)-2-cyclohexylphosphino)ferrocenyl]ethyl bis(2-methylphenyl)-phosphine (=Josiphos SL-J504-2)
(R)-1-[(S)-2-Di-tert.-butylphosphino)ferrocenyl]ethyldicyclohexylphosphine (=Josiphos SL-J505-1)
(S)-1-[(R)-2-di(tert-butyl)phosphino)ferrocenyl]ethyl bis(2-methylphenyl)-phosphine (=Josiphos SL-J505-2)
(R)-1-[(S)-2-di(tert-butyl)phosphino)ferrocenyl]ethyl bis(4-trifluoromethyl)-phosphine (=Josiphos SL-J506-1)

Walphos ligands are for example:
(R)-1-[(R)-2-(2'-Diphenylphosphinophenyl)ferrocenyl]ethyldiphenylphosphine (=Walphos SL-W002-1)
(R)-1-[(R)-2-(2.-Diphenylphosphinophenyl)ferrocenyl]ethyldi(bis-3,5-trifluoromethylphenyl)phosphine (=Walphos SL-W001-1)
(S)-1-[(S)-2-(2.-Diphenylphosphinophenyl)ferrocenyl]ethyldi(bis-3,5-trifluoromethylphenyl)phosphine (=Walphos SL-W001-2)
(R)-1-[(R)-2-(2'-Diphenylphosphinophenyl)ferrocenyl]ethyldicyclohexylphosphine (=Walphos SL-W003-1)
(R)-1-[(R)-2-{2'-Di(3,5-dimethyl-4-methoxyphenyl)-phosphinophenyl}ferrocenyl]ethyldi(bis-3,5-trifluoromethylphenyl)phosphine (=Walphos SL-W005-1)
(R)-1-[(R)-2-(2'-Diphenylphosphinophenyl)ferrocenyl]ethyldi(3,5-xylyl)phosphine (=Walphos SL-W006-1)
(R)-1-[(R)-2-(2'-Dicyclohexylphosphinophenyl)ferrocenyl]ethyldi(bis-(3,5-trifluoromethyl)-phenyl)-phosphine (=Walphos SL-W008-1)
(S)-1-[(S)-2-(2'-Dicyclohexylphosphinophenyl)ferrocenyl]ethyldi(bis-(3,5-trifluoromethyl)-phenyl)-phosphine (=Walphos SL-W008-2)
(R)-1-[(R)-2-(2.-Di-(3,5-xylyl)phosphinophenyl)-ferrocenyl]ethyldi(3,5-xylyl)phosphine (=Walphos SL-W009-1)
(R)-1-[(R)-2-(2'-(Diphenylphosphinophenyl)ferrocenyl] ethyl di(tert-butyl)-phosphine (=Walphos SL-W012-1)
(R)-1-{(R)-2-[4',5'-dimethoxy-2'-(Diphenylphosphino)phenyl]ferrocenyl}ethyl di(bis-(3,5-trifluoromethyl)phenyl)-phosphine (=Walphos SL-W021-1)
(R)-1-{(R)-2-[2'-bis(2-methoxyphenyl)phosphinophenyl]ferrocenyl}ethyl di(bis-(3,5-trifluoromethyl)phenyl)-phosphine (=Walphos SL-W024-1)

Fenphos ligands are for example:
(−)-(R)—N,N-Dimethyl-1-[(S)-1',2-bis(diphenylphosphino)ferrocenyl]ethylamine (=Fenphos SL-F102-1)
(R)—(S)-1-(Dimethylamino-eth-1-yl)-2-difurylphosphino-3-diphenylphosphino-ferrocene (=Fenphos SL-F055-1)
(R)—(S)-1-(Dimethylamino-eth-1-yl)-2-diethylphosphino-3-bis(2-Methoxyphenyl)-phosphino-ferrocene (=Fenphos SL-F056-1)
(R)—(S)-1-(Dimethylamino-eth-1-yl)-2-bis(3,5-dimethyl-4-methoxyphenyl)phosphino-3-dicyclohexylphosphino-ferrocene (=Fenphos SL-F061-1)
(R)—(S)-1-(Dimethylamino-eth-1-yl)-2-bis(4-trifluoromethylphenyl)phosphino-3-dicyclohexylphosphino-ferrocene (=Fenphos SL-F062-1)
(Rc)-(Sp)-(Se)-1,1'-Bis[2-(1-N,N-Dimethylaminoethyl)-1-ferrocenyl]phenylphosphino ferrocene (=Fenphos SL-F131-1)

(Rc)-(Sp)-(Se)-1-{[2-(1-N,N-Dimethylaminoethyl)-1-ferrocenyl]phenylphosphino}-2-{[2-(1-N,N-Dimethylaminoethyl)-1-ferrocenyl]isopropylphosphino}ferrocene (=Fenphos SL-F132-1)

(Rc)-(Sp)-(Se)-1-{[2-(1-N,N-Dimethylaminoethyl)-1-ferrocenyl]phenyl phosphino}-2-{[2-(1-N,N-Dimethylaminoethyl)-1-ferrocenyl]cyclohexylphosphino}ferrocene (=Fenphos SL-F133-1)

(Rc)-(Sp)-(Se)-1,1'-Bis[2-(1-N,N-Dimethylaminoethyl)-1-ferrocenyl]cyclohexyl phosphino ferrocene (=Fenphos SL-F134-1)

(Rc)-(Sp)-(Se)-1,1'-Bis[2-(1-N,N-Dimethylaminoethyl)-1-ferrocenyl]isopropyl phosphino ferrocene (=Fenphos SL-F135-1)

(Rc)-(Sp)-(Se)-1-{[2-(1-N,N-Dimethylaminoethyl)-1-ferrocenyl]phenylphosphino}-1'-{di[bis-(3,5-trifluoromethyl)phenyl]-phosphino}ferrocene (=Fenphos SL-F355-1)

(Rc)-(Sp)-(Se)-1-{[2-(1-N,N-Dimethylaminoethyl)-1-ferrocenyl]phenylphosphino}-1 -(dicyclohexylphosphino)ferrocene (=Fenphos SL-F356-1)

(Rc)-(Sp)-(Se)-1-{[2-(1-N,N-Dimethylanninoethyl)-1-ferrocenyl]cyclohexylphosphino}-1'-(dicyclohexylphosphino) ferrocene (=Fenphos SL-F365-1)

(−)-(R)—N,N-Dimethyl-1-[(S)-1',2-bis(diphenylphosphino)ferrocenyl]ethylamine (=Fenphos SL-F102-1)

(Sc)-(Rp)-(Re)-1-{[2-(1-N,N-Dimethylaminoethyl)-1-ferrocenyl]phenylphosphino}-1'-(dicyclohexylphosphino) ferrocene (=Fenphos SL-F356-2)

Atropisomer ligands are for example:

(S)-(−)-(6,6i-Dimethoxybiphenyl-2,2'-diyl)-bis(diphenylphosphine) (=Atropisomer SL-A101-2)

(R)-(+)-5,5'-Bis(diphenylphosphino)-4,4'-bi-1,3-benzodioxole (=Atropisomer SL-A241-1)

(R)-(+5,5'-Bis[di(3,5-di-t-butyl-4-methoxyphenyl)phosphino]-4,4'-bi-1,3-benzodioxole (=Atropisomer SL-A242-1)

R-(−)-5,5'-Bis(diphenylphosphino)-2,2,2',2'-tetrafluoro-4,4'-bi-1,3-benzodioxole (=Atropisomer SL-A153-1)

S-(−)-5,5'-Bis(diphenylphosphino)-2,2,2',2'-tetrafluoro-4,4'-bi-1,3-benzodioxole (=Atropisomer SL-A153-2)

(S)-(−)-(6,6'-Dimethoxybiphenyl-2,2'-diyl)-bis(di-(4-methylphenyl)phosphine) (=Atropisomer SL-A102-2)

(R)-(6,6'-Dimethoxybiphenyl-2,2'-diyl)-bis(di-(2-furyl)phosphine) (=Atropisomer SL-A108-1)

(S)-(6,6'-Dimethoxybiphenyl-2,2'-diyl)-bis(di-(3,5-dimethylphenyl)phosphine) (=Atropisomer SL-Al20-2)

(S)-(6,6'-Dimethoxybiphenyl-2,2'-diyl)-bis(di-(3,5-di-tert-butylphenyl)phosphine) (=Atropisomer SL-Al21-2)

(S)-(6,6'-O-[1,4-Butylene]-oxybiphenyl-2,2'-diyl)-bis(diphenyl)phosphine (=Atropisomer SL-A152-2)

(S)-(+)-1,13-Bis(diphenylphosphino)-7,8-dihydro-6H-dibenzo[f,h][1,5]dioxonin (=Atropisomer SL-A154-2)

(S)-(+)-5,5'-Bis(diphenylphosphino)-4,4'-bi-1,3-benzodioxole (=Atropisomer SL-A241-2)

(R)-(+)-(6,6'-Dimethoxybiphenyl-2,2'-diyl)-bis(diphenylphosphine) (=Atropisomer SL-A101-1)

(S)-(6,6'-Dimethoxybiphenyl-2,2'-diyl)-bis[bis(3,5-di-tert-butyl-4-methoxyphenyl)phosphine) (=Atropisomer SL-A109-2)

(S)-(6,6'-Dimethoxybiphenyl-2,2'-diyl)bis(diisopropylphosphine) (=Atropisomer SL-A116-2)

(R)-(6,6'-Dimethoxybiphenyl-2,2'-diyl)bis(dicyclobutylphosphine) (=Atropisomer SL-A118-1)

Taniaphos ligands are for example:

(R)-1-Dicyclohexyl-phosphino-2-{(R)-(dimethylamino)[2'-(cyclohexylphosphino)phenyl]methy}ferrocene (=Taniaphos SL-T002-1)

(1S)-Diphenylphosphino-2-[(R)-α-(N,N-dimethylamino)-o-diphenylphosphinophenyl)-methyl]ferrocene (=Taniaphos SL-T001-1)

(1R)-Diphenylphosphino-2-[(S)-α-(N,N-dimethylamino)-o-diphenylphosphinophenyl)-methyl]ferrocene (=Taniaphos SL-T001-2)

(R)-1-bis(4-methoxy-3,5-dimethylphenyl)phosphino-2-{(R)-(dimethylamino)-[2-(bis(4-methoxy-3,5-dimethylphenyl)phosphino)phenyl]methy}ferrocene (=Taniaphos SL-T003-1)

(S)-1-diphenylphosphino-2-[(S)-hydroxy-[2-(diphenylphosphino)phenyl]methyl]ferrocene (=Taniaphos SL-T021-2)

Phospholane ligands are for example:

(1S,1'S,2R,2'R)-(−)-2,2'-Di-t-butyl-2,3,2',3'-tetrahydro-1,1'-bi-1H-isophosphindole (=Phospholane SL-P114-1)

(S,S,S,S)-2,3-Bis(2,5-dimethyl-phospholanyl)benzo[b]thiophene (=Phospholane SL-P005-2)

2-[(2'R,5'R)-2',5'-dimethylphospholano]-1-[(R)-diphenylphosphino]ferrocene (=Phospholane SL-P051-1)

1,2-Bis[(2S,5S)-2,5-dimethylphospholano]ethane (=Phospholane SL-P104-2)

1,2-Bis[(2R,5R)-2,5-diethylphospholano]benzene (=Phospholane SL-P102-1)

(R,R,R,R)-2,3-Bis(2,5-dimethyl-phospholanyl)benzo[b]thiophene (=Phospholane SL-P005-1)

SpiroP ligands are, for example, as described in Chan, Albert S. C.; Hu, Wenhao; Pai, Cheng-Chao; Lau, Chak-Po; Jiang, Yaozhong; Mi, Aiqiao; Yan, Ming; Sun, Jian; Lou, Rongliang; Deng, Jingen, Journal of the American Chemical Society (1997), 119(40), 9570; Hu, Wenhao; Yan, Ming; Lau, Chak-Po; Yang, S. M.; Chan, Albert S. C.; Jiang, Yaozhong; Mi, Aiqiao, Tetrahedron Letters (1999), 40(5), 973, for example, R is Ph. In particular, suitable SpiroP ligands are, for example, (R,R,R)-SpiroP.

1R,5R,6R-(+)-1,6-Bis(diphenylphosphinoxy)spiro[4.4]nonane (=(R,R,R)-SpiroP).

SDP ligands are, for example, as described in Zhou, Qilin; Xie, Jianhua; Cheng, Xu; Fu, Yu; Wang, Lixin. Faming Zhuanli Shenqing Gongkai Shuomingshu (2003), 15 pp. CODEN: CNXXEV CN 1439643 A 20030903 CAN 143: 248512 AN 2005:940880; Xie, Jian-Hua; Wang, Li-Xin; Fu, Yu; Zhu, Shuo-Fei; Fan, Bao-Min; Duan, Hai-Feng; Zhou, Qi-Lin, Journal of the American Chemical Society (2003), 125(15), 4404, for example, R is Ph. In particular, suitable SDP ligands are, for example, (R)-SDP:

(R)-(+)-7,7'-Bis(diphenylphosphino)-2,2',3,3'-tetrahydro-1,1'-spirobiindane (=(R)-SDP)

UbaPHOX ligands are, for example, as described in Pfaltz, Andreas; Blankenstein, Joerg R.; Menges, Frederik; Eur. Pat. Appl. 2002, 42 pp. CODEN: EPXXDW EP 1191030 A2 20020327 CAN 136:279564 AN 2002:237901; Menges, Frederik; Pfaltz, Andreas, Advanced Synthesis & Catalysis (2002), 344(1), 40; Bonrath, Werner; Menges, Frederik; Netscher, Thomas; Pfaltz, Andreas; Wuestenberg, Bettina, PCT Int. Appl. (2006), 48 pp. CODEN: PIXXD2 WO 2006066863 A1 20060629 CAN 145:103859 AN 2006: 634510, for example, R is Ph, R' is benzyl, Ar is Ph. In particular, a suitable Ubaphox ligands are, for example, (S,S)-UbaPHOX:

(4S,5S)-4-(2-(diphenylphosphinooxy)-1,3-diphenylpropan-2-yl)-5-methyl-2-phenyl-4,5-dihydrooxazole (=(S,S)-Ubaphox)

An example of a further suitable chiral ligand is (S)-(6,6'-Dimethylbiphenyl-2,2'-diyl)bis(dicyclohexylphosphine) (=Atropisomer SL-A132-2).

In a first embodiment, the reduction of the compound of formula (5a), or salt thereof, provides a composition comprising the compounds according to formulae (2a) and (2b), or salts thereof, wherein the molar ratio of compounds according to formula (2a), or salts thereof, to compounds according to formula (2b), or salts thereof, is at least 55 to 45, preferably at least 80 to 20, more preferably at least 90 to 10, even more preferably at least 99 to 1. In this first embodiment, suitable chiral ligands are, for example, an Atropisomer, Fenphos, Josiphos, Mandyphos, Taniaphos, Walphos, BINAP, ChiraPhos, DIOP, BDPP, PhanePhos or (R)-SDP Chiral Ligand; more preferably, an Atropisomer, Fenphos, Josiphos, Mandyphos, Taniaphos, Walphos, DIOP or PhanePhos Chiral Ligand; even more preferably, an Atropisomer, Fenphos, Walphos or PhanePhos Chiral Ligand; yet more preferably the chiral ligand is SL-A101-2, SL-A109-2, SL-A241-1, SL-F102-1, SL-F356-1, SL-J003-1, SL-J005-2, SL-J216-1, SL-J226-2, SL-J302-1, SL-J504-1, SL-J505-1, SL-J505-2, SL-M001-1, SL-M002-2, SL-M003-1, SL-M004-1, SL-M004-2, SL-T001-1, SL-T002-1, SL-W001-1, SL-W008-1, SL-W008-2, (R)-Xyl-BINAP, (R,R)-ChiraPhos, (R,R)-MOD-DIOP, (R,R)-BDPP, (R,R)-PhanePhos or (R)-SDP; still more preferably, the chiral ligand is SL-A101-2, SL-A109-2, SL-A241-1, SL-F356-1, SL-J003-1, SL-J005-2, SL-J216-1, SL-J302-1, SL-M001-1, SL-M002-2, SL-M003-1, SL-T001-1, SL-T002-1, SL-W008-1, (R,R)-MOD-DIOP or (R)-PhanePhos. Even more preferably, the chiral ligand is SL-A101-2, SL-F356-1, SL-W008-1 or (R)-PhanePhos. In particular, the transition metal catalyst comprises an organometallic complex and a chiral ligand, for example, wherein the rhodium organometallic complex is selected from [Rh(cod)$_2$]O$_3$SCF$_3$ and [Rh(nbd)$_2$]BF$_4$ and the chiral ligand is selected from; SL-A101-2, SL-A109-2, SL-A241-1, (R,R)-MOD-DIOP, (R)-PhanePhos, SL-F356-1, SL-J003-1, SL-J005-2, SL-J216-1, SL-J302-1, SL-M001-1, SL-M002-2, SL-M003-1, SL-T001-1, SL-T002-1 and SL-W008-1; or the ruthenium organometallic complex is [Ru(cod)(OOCCF$_3$)$_2$] and the chiral ligand is selected from (R)-PhanePhos and SL-M002-2.

In this first embodiment, particularly suitable transition metal catalysts are for example: [Rh(cod)(SL-P005-1)]BF$_4$, [Rh(cod)(SL-P114-1)]BF$_4$ or [Rh(cod)(SL-P102-1)]O$_3$SCF$_3$. When using these catalysts, the reduction of the compound of formula (5a), or salt thereof, provides a composition comprising the compounds according to formulae (2a) and (2b), or salts thereof, wherein the molar ratio of compounds according to formula (2a), or salts thereof, to compounds according to formula (2b), or salts thereof, is at least 51:49, preferably at least 61:39.

In a second embodiment, the reduction of the compound of formula (5a), or salt thereof, provides a composition comprising the compounds according to formulae (2a) and (2b), or salts thereof, wherein the molar ratio of compounds according to formula (2b), or salts thereof, to compounds according to formula (2a), or salts thereof, is at least 55 to 45, preferably at least 80 to 20, more preferably at least 95 to 5. In this second embodiment, suitable chiral ligands are, for example, Atropisomer, Josiphos, Mandyphos, Taniaphos, Walphos, BINAP, ChiraPhos, BDPP, PhanePhos or SDP Chiral Ligand; preferably, an Atropisomer ligand or (R,R)-BDPP; even more preferably, SL-A101-1, SL-A241-1, SL-A242-1, SL-J003-1, SL-J005-2, SL-J216-1, SL-J226-2, SL-J302-1, SL-M002-2, SL-M004-1, SL-M004-2, SL-T001-1, SL-W008-1, SL-W008-2, (R)-Xyl-BINAP, (R,R)-ChiraPhos, (R,R)-BDPP, (R)-PhanePhos or (R)-SDP; still more preferably, SL-A242-1 or (R,R)-BDPP. In particular, the transition metal catalyst comprises an organometallic complex and a chiral ligand, for example: a rhodium organometallic complex, as defined herein, and the ligand SL-A242-1 or a ruthenium organometallic complex, as defined herein, and a ligand selected from SL-A242-1 or (R,R)-BDPP.

A particularly suitable transition metal catalyst is for example [Rh(cod)(SL-P102-1)]O$_3$SCF$_3$.

All the ligands above-mentioned are commercially available from Johnson Matthey plc (London, United Kingdom) and/or from Solvias AG (Basel, Switzerland).

Section A.2:

In a second aspect, the invention relates to a process to convert a compound of formula (3), or salt thereof, as defined herein, into a compound of formula (2), or salt thereof, as defined herein, as outlined in Scheme 2 above, wherein compounds of formula (4) and (5) are as defined herein. Intermediate process steps described in sections A.2.1, A.1.2 and A.1.3 are also embodiments of the present invention.

Section A.2.1: Synthesis of a Compound of Formula (2)

In another embodiment, the present invention relates to a process for preparing a compound of formula (4), or salt thereof,

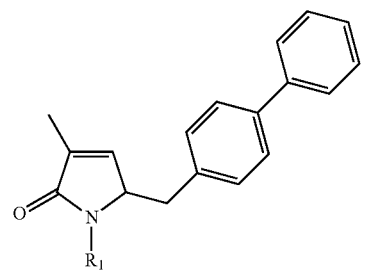

(4)

wherein
R1 is hydrogen or a nitrogen protecting group;
said process comprising
i) reacting a compound of formula (3), or salt thereof,

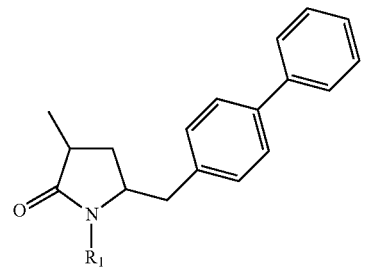

(3)

wherein R1 is hydrogen or a nitrogen protecting group;
with a selenide in the presence of a base,
to obtain a compound of formula (6), or salt thereof,

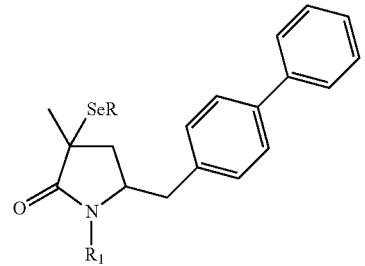

(6)

wherein R1 is hydrogen or a nitrogen protecting group; and R is aryl; and ii) treating the compound of formula (6) with an oxidizing agent, to obtain the compound of formula (4).

In a preferred embodiment, the present invention relates to a process for preparing a compound of formula (4a), or salt thereof,

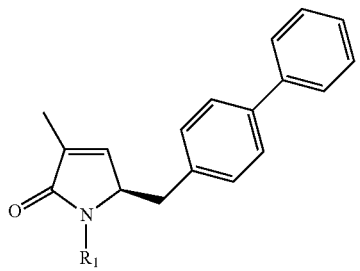

(4a)

wherein
R1 is hydrogen or a nitrogen protecting group;
said process comprising
  i) reacting a compound of formula (3a), or salt thereof,

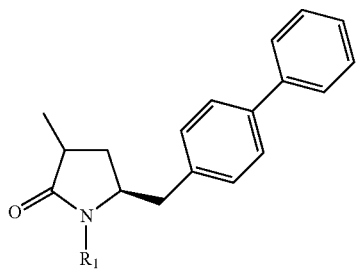

(3a)

wherein R1 is hydrogen or a nitrogen protecting group;
with a selenide in the presence of a base,
to obtain a compound of formula (6a), or salt thereof,

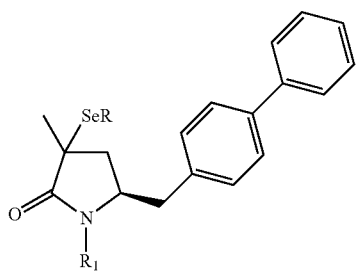

(6a)

wherein R1 is hydrogen or a nitrogen protecting group; and R is aryl; and ii) treating the compound of formula (6a) with an oxidizing agent,
to obtain the compound of formula (4a).

A compound of formula (3), preferably of formula (3a), can be obtained according to methods known in the art, for example as described in WO2008/083967.

Suitable selenides are, for example, selenides of formula RSeX, wherein R is aryl and X is halo, for example RSeX is phenylselenyl bromide, phenylselenyl chloride or phenylselenyl iodide; preferably phenylselenyl bromide.

Suitable bases are, for example,
  a base of the formula RcRdNM, wherein Rc and Rd are independently selected from alkyl, cycloalkyl, heterocyclyl or silyl and M is an alkali metal (eg lithium, sodium, potassium), for example RcRdNM is lithium bis(trimethylsilyl)amide (LHMDS), sodium bis(trimethylsilyl)amide (NaHMDS), potassium bis(trimethylsilyl)amide (KHMDS), lithium diisopropylamide (LDA) or potassium diisopropylamide;
  a base of the formula MRa, wherein M is an alkali metal (eg lithium, sodium, potassium) and Ra is alkyl or aryl, for example MRa is methyl lithium, n-butyllithium, sec-butyllithium, tert-butyllithium or phenyllithium;
  metal hydrides, such as alkali metal hydrides (eg sodium hydride, lithium hydride or potassium hydride);
  a base of the formula XMRd, wherein M is magnesium, X is halo and Rd is selected from alkyl, cycloalkyl, heterocyclyl or silyl, for example XMRd is isopropylmagnesium chloride; or
  mixtures thereof.

In one embodiment, the base is sodium hydride, potassium bis(trimethylsilyl)amide (KHMDS), or mixtures thereof.

In step ii) above, the selenide compound of formula (6), preferably of formula (6a), is oxidized to the corresponding selenoxide, which undergoes in-situ elimination to provide the compound of formula (4), preferably of formula (4a). In this step, oxidizing agents well known in the art for converting selenides into selenoxides may be used, for example oxidizing agents as described in Richard C. Larock, "Comprehensive Organic Transformations: A Guide to Functional Group Preparations", VCH Publishers, Inc, $2^{nd}$ Edition, 1999, in particular as described on pages 281, 287 to 289 and 1304, and in the references cited therein; for example it may be effected by the use of hydrogen peroxide, lithium hydrogen peroxide or 3-chloroperbenzoic acid; in particular hydrogen peroxide.

Section A.3:
In a third aspect, the invention relates to a process to convert a compound of formula (4), or salt thereof, as defined herein, into a compound of formula (2), or salt thereof, as defined herein, as outlined in Scheme 3 above, wherein compounds of formula (3) are as defined herein. The intermediate process step described in Section A.3.1 is also an embodiment of the present invention.

Section A.3.1: Reduction of a Compound of Formula (4)
In another embodiment, the subject-matter of the present invention relates to a process for preparing a compound according to formula (3),

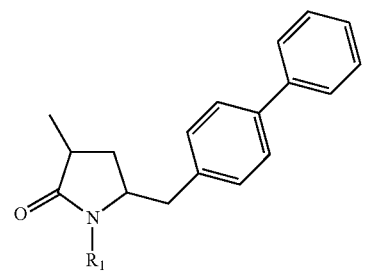

(3)

or salt thereof,
wherein R1 is hydrogen or a nitrogen protecting group, comprising reducing a compound according to formula (4),

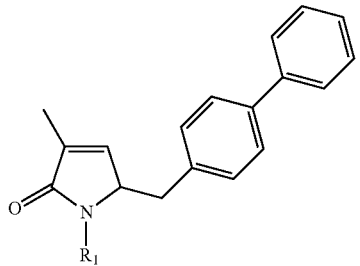

(4)

or salt thereof,
wherein R1 is hydrogen or a nitrogen protecting group, to obtain the compound of formula (3).

Preferably, a compound according to formula (4a), or salt thereof,

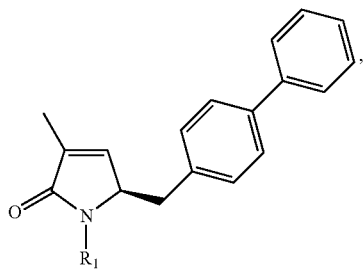

(4a)

wherein R1 is defined as above, is used, which thus leads upon reduction to compounds according to formula (3a)

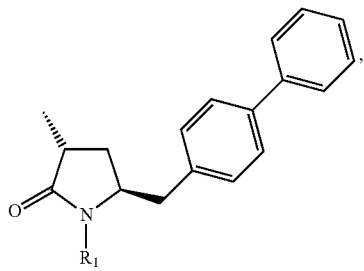

(3a)

and formula (3b),

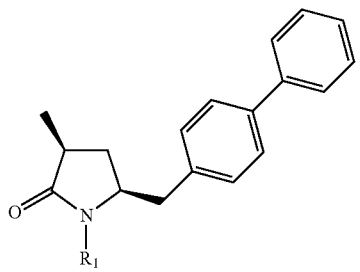

(3b)

or salts thereof, wherein R1 is defined as above.

In a preferred embodiment, the present invention relates to a process for preparing a compound according to formula (3a),

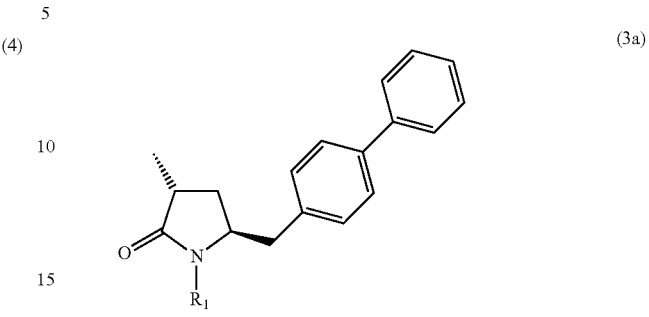

(3a)

or salt thereof,
wherein R1 is hydrogen or a nitrogen protecting group, comprising reducing a compound according to formula (4a),

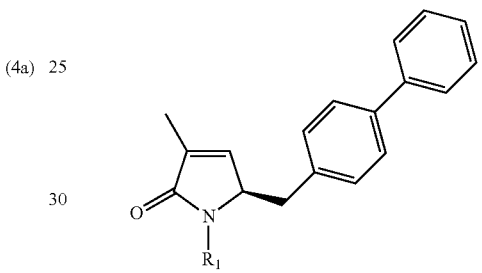

(4a)

or salt thereof,
wherein R1 is hydrogen or a nitrogen protecting group, to obtain the compound of formula (3a).

Preferably, the reduction of the compound of formula (4), or salt thereof, preferably of formula (4a), takes place with hydrogen in the presence of a transition metal catalyst. The transition metal catalyst comprises an organometallic complex and a chiral ligand or is an organometallic catalyst.

The reduction may occur under hetereo- or homogeneous hydrogenation conditions, preferably under heterogeneous hydrogenation conditions.

Generally, the heterogeneous hydrogenation is carried out in the presence of a transition metal catalyst on a solid support, wherein the transition metal is selected from group 9 or 10 of the periodic table. Therefore, the transition metal catalyst comprises, for example, Cobalt (Co), Rhodium (Rh), Iridium (Ir), Nickel (Ni), Palladium (Pd) and/or Platinum (Pt). Solid supports are, for example, carbon, metal oxides (e.g. aluminium oxide, zirconium oxide, titanium oxide or silicon dioxide/aluminium oxide), sulfates (e.g. barium sulfate) or carbonates (e.g. calcium carbonate and barium carbonate). The loading of the transition metal on the solid support is, for example, of from 1% to 10% w/w. In one embodiment, the transition metal catalyst may contain water, for example, of from 0 mass % to 50 mass % content of water. In particular, the transition metal catalyst is Pt, Pd, or Rh on a solid support, such as carbon. In one embodiment the transition metal catalyst is Pd on carbon.

The heterogeneous hydrogenation is usually performed in a solvent, such as ether solvents (eg THF), ester solvents (eg isopropyl acetate) or alcohol solvents (eg isopropanol, ethanol or methanol); in particular isopropyl acetate and ethanol.

In one embodiment, under heterogeneous hydrogenation conditions, a suitable transition metal catalyst is, for example, Pd or Rh on carbon. Under this conditions, the reduction of the compound of formula (4a), or salt thereof, wherein R1 is as defined as above, preferably R1=t-butoxycarbonyl (BOC), provides a composition comprising the compounds according to formulae (3a) and (3b), or salts thereof, wherein the molar ratio of compounds according to formula (3a), or salts thereof, to compounds according to formula (3b), or salts thereof, is at least 17 to 83.

In another embodiment, under heterogeneous hydrogenation conditions, a suitable transition metal catalyst is, for example, Pt on carbon. Under this conditions, the reduction of the compound of formula (4a), or salt thereof, wherein R1 is defined as above, preferably R1=BOC, provides a composition comprising the compounds according to formulae (3a) and (3b), or salts thereof, wherein the molar ratio of compounds according to formula (3b), or salts thereof, to compounds according to formula (3a), or salts thereof, is at least 99 to 1.

Generally, the homogeneous hydrogenation is carried out in the presence of a transition metal catalyst, wherein the transition metal is selected from group 7, 8 or 9 of the periodic table. Therefore, the transition metal catalyst comprises, for example, the transition metal Manganese (Mn), Rhenium (Re), Iron (Fe), Ruthenium (Ru), Osmium (Os), Cobalt (Co), Rhodium (Rh) and/or Iridium (Ir).

The transition metal catalyst comprises an organometallic complex and a chiral ligand, as described in Section A.1.3 above, or is an organometallic catalyst as described in Section A.1.3 above.

In one embodiment, the organometallic complexes is a ruthenium organometallic complex, such as [RuI$_2$(p-cymene)]$_2$, [RuCl$_2$(p-cymene)]$_2$, [Ru(cod)(2-metallyl)$_2$] or [Ru(cod)(OOCCF$_3$)$_2$]; a rhodium organometallic complex, such as [Rh(nbd)$_2$BF$_4$], [Rh(cod)$_2$]O$_3$SCF$_3$ or [Rh(cod)$_2$]BF$_4$; or an iridium organometallic complex such as [(Cy$_3$P)Ir(pyr)]Cl, [Ir(cod)$_2$]BArF or [Ir(cod)$_2$Cl]$_2$.

Suitable chiral ligands are ligands described in Section A.1.3 above, in particular, phospholane ligands, BoPhoz ligands, BINAP ligands, BINOL ligands, P-Phos ligands, ProPhos ligands, BDPP ligands, DIOP ligands, DIPAMP ligands, DuanPhos ligands, NorPhos ligands, BINAM ligands, CatASium ligands, SimplePHOX ligands, PHOX ligands, ChiraPhos ligands, Ferrotane ligands, BPE ligands, TangPhos ligands, JafaPhos ligands, DuPhos ligands, Binaphane ligands, QuinaPhos ligands, Atropisomer ligands, Fenphos ligands, Josiphos ligands, Mandyphos ligands, Taniaphos ligands, Walphos ligands, PhanePhos, UbaPHOX, SpiroP or (R)-SDP ligand.

In a first embodiment, the reduction of the compound of formula (4a), or salt thereof, provides a composition comprising the compounds according to formulae (3a) and (3b), or salts thereof, wherein the molar ratio of compounds according to formula (3a), or salts thereof, to compounds according to formula (3b), or salts thereof, is at least 51 to 49. In this first embodiment, a suitable chiral ligands is, for example, a Mandyphos Ligand such as SL-M004-1. In particular, the transition metal catalyst comprises an organometallic complex and a chiral ligand, for example, a rhodium organometallic complex, as described above, such as [Rh(nbd)$_2$]BF$_4$ or [Rh(cod)$_2$]O$_3$SCF$_3$, and a ligand, such as a Mandyphos ligand, for example SL-M004-1.

In a second embodiment, the reduction of the compound of formula (4a), or salt thereof, provides a composition comprising the compounds according to formulae (3a) and (3b), or salts thereof, wherein the molar ratio of compounds according to formula (3b), or salts thereof, to compounds according to formula (3a), or salts thereof, is at least 51 to 49, preferably at least 80 to 20, more preferably at least 90 to 10, yet more preferably at least 97 to 3. In this second embodiment, suitable chiral ligands are, for example, Atropisomer, Josiphos, Mandyphos, Taniaphos, Walphos, BINAP, PhanePhos or SpiroP ligand; preferably, an Atropisomer, Josiphos, Manndyphos, Taniaphos, PhanePhos or SpiroP ligand; even more preferably, SL-A101-1, SL-A101-2, SL-A109-2, SL-A153-1, SL-J002-2, SL-J005-1, SL-J302-1, SL-J505-1, SL-M004-1, SL-M004-2, SL-T001-1, SL-T002-1, SL-W001-1, SL-W008-1, SL-W008-2, (S)-BINAP, (R)-PhanePhos or (R,R,R)-SpiroP; in particular SL-A101-1, SL-A109-2, SL-J002-2, SL-J302-1, SL-J505-1, SL-M004-2, SL-T002-1, (R)-PhanePhos or (R,R,R)-SpiroP. A particularly suitable transition metal catalyst is for example [Rh(cod)(SL-P102-1)]O$_3$SCF$_3$. [Ir(cod)((S,S)-UbaPHOX)]BARF, [Rh(cod)(SL-P005-2)]BF$_4$, [Rh(cod)(SL-P102-1)]BF$_4$ or [Rh(cod)(SL-P104-2)]O$_3$SCF$_3$; preferably, [Ir(cod)((S,S)-UbaPHOX)]BARF, [Rh(cod)(SL-P005-2)]BF$_4$, [Rh(cod)(SL-P102-1)]BF$_4$ or [Rh(cod)(SL-P104-2)]O$_3$SCF$_3$.

In particular, the transition metal catalyst comprises an organometallic complex and a chiral ligand, for example, wherein
  the rhodium organometallic complex is selected from [Rh(cod)$_2$]O$_3$SCF$_3$, and [Rh(nbd)$_2$]BF$_4$ and the chiral ligand is selected from SL-A109-2, (R,R,R)-SpiroP, SL-J002-2 and SL-T002-1;
  the ruthenium organometallic complex is selected from [Ru(cod)(OOCCF$_3$)$_2$] and [RuCl$_2$(p-cymene)]$_2$ and the chiral ligand is selected from SL-A101-1, (R)-PhanePhos, SL-J302-1, SL-J505-1 and SL-M004-2; or
  the iridium organometallic complex is for example [Ir(cod)$_2$]BARF and the chiral ligand is for example SL-T002-1.

General Terms:

The general definitions used above and below, unless defined differently, have the following meanings:

The term "ester group" comprises any ester of a carboxyl group generally known in the art; for example groups —COOR, wherein R is selected from the group consisting of: C$_{1-6}$alkyl, such as methyl, ethyl or t-butyl, C$_{1-6}$alkoxy C$_{1-6}$alkyl, heterocyclyl, such as tetrahydrofuranyl, C$_{6-10}$aryloxyC$_{1-6}$alkyl, such as benzyloxymethyl (BOM), silyl, such as trimethylsilyl, t-butyldimethylsilyl and t-butyldiphenylsilyl, cinnamyl, allyl, C$_{1-6}$alkyl which is mono-, di- or trisubstituted by halogen, silyl, cyano or C$_{1-6}$aryl, wherein the aryl ring is unsubstituted or substituted by one, two or three, residues selected from the group consisting of C$_{1-7}$alkyl, C$_{1-7}$alkoxy, halogen, nitro, cyano and CF$_3$; or C$_{1-2}$alkyl substituted by 9-fluorenyl. In a preferred embodiment, the "ester group" is —COOR, wherein R is a C$_{1-6}$alkyl residue. In particular, R is methyl or ethyl.

The term "nitrogen protecting group" comprises any group which is capable of reversibly protecting a nitrogen functionality, preferably an amine and/or amide functionality. Preferably the nitrogen protecting group is an amine protecting group and/or an amide protecting group. Suitable nitrogen protecting groups are conventionally used in peptide chemistry and are described e.g. in the relevant chapters of standard reference works such as J. F. W. McOmie, "Protective Groups in Organic Chemistry", Plenum Press, London and New York 1973, in P. G. M. Wuts and T. W. Greene, "Greene's Protective Groups in Organic Synthesis', Fourth Edition, Wiley, New Jersey, 2007, in "The Peptides"; Volume 3 (editors: E. Gross and J. Meienhofer), Academic Press, London and New York 1981, and in "*Methoden der*

*or-ganischen Chemie*" (Methods of Organic Chemistry), Houben Weyl, 4th edition, Volume 15/I, Georg Thieme Verlag, Stuttgart 1974.

Preferred nitrogen protecting groups generally comprise: $C_1$-$C_6$-alkyl, preferably $C_1$-$C_4$-alkyl, more preferably $C_1$-$C_2$-alkyl, most preferably $C_1$-alkyl which is mono-, di- or tri-substituted by trialkylsilyl$C_1$-$C_7$-alkoxy (eg. trimethylsilylethoxy), aryl, preferably phenyl, or an heterocyclic group, preferably pyrrolidinyl, wherein the aryl ring or the heterocyclic group is unsubstituted or substituted by one or more, e.g. two or three, residues, e.g. selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$; aryl-C1-C2-alkoxycarbonyl (preferably phenyl-C1-C2-alkoxycarbonyl eg. benzyloxycarbonyl); $C_{1-10}$alkenyloxycarbonyl; $C_{1-6}$alkylcarbonyl (eg. acetyl or pivaloyl); $C_{6-10}$arylcarbonyl; $C_{1-6}$alkoxycarbonyl (eg. t-butoxycarbonyl); $C_{6-10}$aryl$C_{1-6}$alkoxycarbonyl; allyl or cinnamyl; sulfonyl or sulfenyl; succinimidyl group, silyl, e.g. triarylsilyl or trialkylsilyl (eg. triethylsilyl).

Examples of preferred nitrogen protecting groups are acetyl, benzyl, cumyl, benzhydryl, trityl, benzyloxycarbonyl (Cbz), 9-fluorenylmethyloxycarbony (Fmoc), benzyloxymethyl (BOM), pivaloyl-oxy-methyl (POM), trichloroethoxycarbonyl (Troc), 1-adamantyloxycarbonyl (Adoc), allyl, allyloxycarbonyl, trimethylsilyl, tert.-butyldimethylsilyl, triethylsilyl (TES), triisopropylsilyl, trimethylsilylethoxymethyl (SEM), t-butoxycarbonyl (BOC), t-butyl, 1-methyl-1, 1-dimethylbenzyl, (phenyl)methylbenzene, pyrridinyl and pivaloyl. Most preferred nitrogen protecting groups are acetyl, benzyl, benzyloxycarbonyl (Cbz), triethylsilyl (TES), trimethylsilylethoxymethyl (SEM), t-butoxycarbonyl (BOC), pyrrolidinylmethyl and pivaloyl. Preferably the nitrogen protecting group is BOC.

Examples of more preferred nitrogen protecting groups are pivaloyl, pyrrolidinylmethyl, t-butoxycarbonyl, benzyl and silyl groups, particularly silyl groups according to the formula SiR11R12R13, wherein R11, R12 and R13 are, independently of each other, alkyl or aryl. Preferred examples for R11, R12 and R13 are methyl, ethyl, isopropyl, t-butyl and phenyl.

Particularly preferred nitrogen protecting groups are pivaloyl and t-butoxycarbonyl (BOC).

Alkyl being a radical or part of a radical is a straight or branch (one or, if desired and possible, more times) carbon chain, and is especially $C_1$-$C_7$-alkyl, preferably $C_1$-$C_4$-alkyl.

The term "$C_1$-$C_7$-" defines a moiety with up to and including maximally 7, especially up to and including maximally 4, carbon atoms, said moiety being branched (one or more times) or straight-chained and bound via a terminal or a non-terminal carbon Cycloalkyl is, for example, $C_3$-$C_7$-cycloalkyl and is, for example, cyclopropyl, cyclobutyl, cyclopentyl, cyclohexyl and cycloheptyl. Cyclopentyl and cyclohexyl are preferred.

Alkoxy being a radical or part of a radical is, for example, $C_1$-$C_7$-alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$-$C_4$alkoxy is preferred.

Alkanoyl is, for example, $C_2$-$C_5$-alkanoyl and is, for example, acetyl [—C(=O)Me], propionyl, butyryl, isobutyryl or pivaloyl. $C_2$-$C_5$-Alkanoyl is preferred, especially acetyl.

Halo or halogen is preferably fluoro, chloro, bromo or iodo, most preferably, chloro, bromo, or iodo.

Halo-alkyl is, for example, halo-$C_1$-$C_7$alkyl and is in particular halo-$C_1$-$C_4$alkyl, such as trifluoromethyl, 1,1,2-trifluoro-2-chloroethyl or chloromethyl. Preferred halo-$C_1$-$C_7$alkyl is trifluoromethyl.

Alkenyl may be linear or branched alkyl containing a double bond and comprising preferably 2 to 12 C atoms, 2 to 10 C atoms being especially preferred. Particularly preferred is a linear $C_{2-4}$alkenyl. Some examples of alkyl groups are ethyl and the isomers of propyl, butyl, pentyl, hexyl, heptyl, octyl, nonyl, decyl, undecyl, dodecyl, tetradecyl, hexadecyl, octacyl and eicosyl, each of which containing a double bond. Especially preferred is allyl.

Alkylene is a bivalent radical derived from $C_{1-7}$alkyl and is especially $C_2$-$C_7$-alkylene or $C_2$-$C_7$-alkylene and, optionally, can be interrupted by one or more, e.g. up to three, O, NR14 or S, wherein R14 is alkyl, each of which can be unsubstituted or substituted, by one or more substituents independently selected from for example, $C_1$-$C_7$-alkyl, $C_1$-$C_7$-alkoxy-$C_1$-$C_7$-alkyl or $C_1$-$C_7$-alkoxy.

Alkenylene is a bivalent radical derived from $C_{2-7}$alkenyl and can be interrupted by, one or more, e.g. up to three, O, NR14 or S, wherein R14 is alkyl, and is unsubstituted or substituted by one or more, e.g. up to three, substitutents preferably independently selected from the substitutents mentioned above for alkylene.

Aryl being a radical or part of a radical is, for example $C_{6-10}$aryl, and is, preferably a mono- or polycyclic, especially monocyclic, bicyclic or tricyclic aryl moiety with 6 to 10 carbon atoms, preferably phenyl, and which can be unsubstituted or substituted, by one or more substituents independently selected from for example, $C_1$-$C_7$-alkyl, $C_1$-$C_7$alkoxy-$C_1$-$C_7$-alkyl or $C_1$-$C_7$-alkoxy.

The term arylalkyl refers to aryl-$C_1$-$C_7$-alkyl, wherein aryl is as defined herein and is for example benzyl.

The term carboxyl refers to —$CO_2H$.

Aryloxy refers to a Aryl-O— wherein aryl is as defined above.

Unsubstituted or substituted heterocyclyl is a mono- or polycyclic, preferably a mono-, bi- or tricyclic-, most preferably mono-, unsaturated, partially saturated, saturated or aromatic ring system with preferably 3 to 14 (more preferably 5 to 14) ring atoms and with one or more, preferably one to four, heteroatoms independently selected from nitrogen, oxygen, sulfur, S(=O)— or S—(=O)$_2$, and is unsubstituted or substituted by one or more, e.g. up to three, substitutents preferably independently selected from the group consisting of halo, $C_1$-$C_7$-alkyl, $C_1$-$C_7$-alkoxy, halo-$C_1$-$C_7$-alkoxy, such as trifluoromethoxy and $C_1$-$C_7$-alkoxy-$C_1$-$C_7$-alkoxy. When the heterocyclyl is an aromatic ring system, it is also referred to as heteroaryl.

Acetyl is —C(=O)$C_1$-$C_7$alkyl, preferably —C(=O)Me.

Silyl is —SiRR'R", wherein R, R' and R" are independently of each other $C_{1-7}$alkyl, aryl or phenyl-$C_{1-4}$alkyl.

Sulfonyl is (unsubstituted or substituted) $C_1$-$C_7$-alkylsulfonyl, such as methylsulfonyl, (unsubstituted or substituted) phenyl- or naphthyl-$C_1$-$C_7$-alkylsulfonyl, such as phenylmethanesulfonyl, or (unsubstituted or substituted) phenyl- or naphthyl-sulfonyl; wherein if more than one substituent is present, e.g. one to three substitutents, the substituents are selected independently from cyano, halo, halo-$C_1$-$C_7$alkyl, halo-$C_1$-$C_7$-alkyloxy- and $C_1$-$C_7$-alkyloxy. Especially preferred is $C_1$-$C_7$-alkylsulfonyl, such as methylsulfonyl, and (phenyl- or naphthyl)-$C_1$-$C_7$-alkylsulfonyl, such as phenylmethanesulfonyl.

Sulfenyl is (unsubstituted or substituted) $C_{6-10}$aryl-$C_1$-$C_7$-alkylsulfenyl or (unsubstituted or substituted) $C_{6-10}$arylsulfenyl, wherein if more than one substituent is present, e.g.

one to four substitutents, the substituents are selected independently from nitro, halo, halo-$C_1$-$C_7$alkyl and $C_1$-$C_7$-alkyloxy.

A "heterogeneous" catalyst as used herein refers to a catalyst supported on a carrier, typically although not necessarily a substrate comprised of an inorganic material, for example, a porous material such as carbon, silicon and/or aluminum oxide. In one embodiment, the heterogeneous catalyst is a hydrogenation catalyst, in particular those described in Sections A.1.3 and A.3.1.

A "homogeneous" catalyst as used herein refers to a catalyst that is not supported on a carrier. In one embodiment, the homogeneous catalyst is a hydrogenation catalyst, in particular those described in Sections A.1.3 and A.3.1.

The term "transition metal catalyst" refers to an organometallic catalyst, an organometallic complex or an organometallic complex and a chiral ligand. Transition metal catalysts are in particular those described in Sections A.1.3 and A.3.1.

The term "organometallic complex" refers to complexes derived from a transition metal and one or more (for example up to four) achiral (non chiral) ligands; for example, ruthenium organometallic complexes, such as $[RuI_2(p\text{-cymene})]_2$, $[RuCl_2(p\text{-cymene})]_2$, $[Ru(cod)(2\text{-metal-lyl})_2]$ or $[Ru(cod)(OOCCF_3)_2]$; rhodium organometallic complexes, such as $[Rh(nbd)_2]BF_4$ or $[Rh(cod)_2]BF_4$; or an iridium organometallic complexes, such as $[(Cy_3P)Ir(pyr)]Cl$ or $[Ir(cod)_2Cl]_2$.

The term "organometallic catalyst" refers to a catalysts derived from a transition metal and one or more (for example up to four) chiral ligands.

The term "ligand" means any compound, achiral or chiral, that can form a complex with a transition metal. Chiral and achiral ligands are in particular those described in Sections A.1.3 and A.3.1.

The term "catalyst" means any substance that affects the rate of a chemical reaction by lowering the activation energy for the chemical reaction.

The term "powder" means a catalyst having a water contain of from 0 to 30 mass %.

The term "substrate to catalyst ratio" (S/C) refers to the molar ratio of starting compounds, or salts thereof, to "transition metal catalyst".

The term "chiral" refers to molecules which have the property of non-superimposability on their mirror image partner, while the term "achiral" refers to molecules which are superimposable on their mirror image partner.

The term "tautomer" refers in particular to the enol tautomer of the pyrrolidin-2-one moiety of the compounds of the present invention. Additionally, the term "tautomer" also refers in particular to the aldehyde tautomer of compounds of the present invention, where such compounds can exists in either an enol or aldehyde form, or mixtures thereof.

In the formulae of the present application the term "⌇" or "⌇" on a C-sp³ represents a covalent bond wherein the stereochemistry of the bond is not defined. This means that the term "⌇" or "⌇" on a C-sp³ comprises an (S) configuration as well as an (R) configuration of the respective chiral centre. Furthermore, mixtures are also encompassed, e.g., mixtures of enantiomers, such as racemates, are encompassed by the present invention.

In the formulae of the present application the term "⌇" on a C-sp² represents a covalent bond, wherein the stereochemistry or the geometry of the bond is not defined. This means that the term "⌇" on a C-sp² comprises a cis (Z) configuration as well as a trans (E) configuration of the respective double bond. Furthermore, mixtures are also encompassed, e.g., mixtures of double bond isomers are encompassed by the present invention.

The compounds of the present invention can possess one or more asymmetric centers. The preferred absolute configurations are as indicated herein specifically.

In the formulae of the present application the term "∕" on a C-sp³ indicates the absolute stereochemistry, either (R) or (S).

In the formulae of the present application the term "∕" on a C-sp³ indicates the absolute stereochemistry, either (R) or (S).

In the formulae of the present application, the term "═" indicates a $Csp^3$-$Csp^3$ bond or a $Csp^2$-$Csp^2$ bond.

Salts are especially pharmaceutically acceptable salts or generally salts of any of the intermediates mentioned herein, where salts are not excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, any of the intermediates mentioned herein may also form internal salts.

For isolation or purification purposes of any of the intermediates mentioned herein it is also possible to use pharmaceutically unacceptable salts, for example picrates or perchlorates.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter is to be understood as referring also to one or more salts thereof or a mixture of a corresponding free compound, intermediate or starting material and one or more salts thereof, each of which is intended to include also any solvate or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is not intended to exclude the plural, but only preferably means "one".

Any of the lactams according to the present invention, or salts thereof, wherein R1 is hydrogen can be converted into a corresponding protected lactam, or salt thereof, wherein R1 is a nitrogen protecting group, as defined above, according to standard methods of organic chemistry known in the art, in particular reference is made to conventional nitrogen protecting group methods described in J. F. W. McOmie, "Protective Groups in Organic Chemistry", Plenum Press, London and New York 1973, in P. G. M. Wuts and T. W. Greene, "Greene's Protective Groups in Organic Synthesis', Fourth Edition, Wiley, New Jersey, 2007 and in Richard C. Larock, "Comprehensive Organic Transformations: A Guide to Functional Group Preparations", Second Edition, Wiley-VCH Verlag GmbH, 2000, in particular, in the relevant chapters thereof.

Analogously, any of the lactams according to the present invention, or salt thereof, wherein R1 is a nitrogen protecting group, can be converted into the corresponding lactam, or salt thereof, wherein R1 is a hydrogen, according to standard methods of organic chemistry known in the art, in particular reference is made to conventional nitrogen protecting group methods described in the books mentioned above, in particular, in the relevant sections.

The term "prodrug," as used herein, represents in particular compounds which are transformed in vivo to the parent compound, for example, by hydrolysis in blood, for example as described in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987; H Bundgaard, ed, Design of Prodrugs, Elsevier, 1985; and Judkins, et al. Synthetic Communications, 26(23), 4351-4367 (1996), and "The Organic Chemistry of Drug Design and Drug Action", $2^{nd}$ Edition, R B Silverman (particularly Chapter 8, pages 497 to 557), Elsevier Academic Press, 2004.

Prodrugs therefore include drugs having a functional group which has been transformed into a reversible derivative thereof. Typically, such prodrugs are transformed to the active drug by hydrolysis. As examples may be mentioned the following:

| Functional Group | Reversible derivative |
| --- | --- |
| Carboxylic acid | Esters, including e.g. alkyl esters |
| Alcohol | Esters, including e.g. sulfates and phosphates as well as carboxylic acid esters |
| Amine | Amides, carbamates, imines, enamines, |
| Carbonyl (aldehyde, ketone) | Imines, oximes, acetals/ketals, enol esters, oxazolidines and thiazoxolidines |

Prodrugs also include compounds convertible to the active drug by an oxidative or reductive reaction. As examples may be mentioned:

Oxidative activation
N- and O- dealkylation
Oxidative deamination
N-oxidation
Epoxidation
Reductive activation
Azo reduction
Sulfoxide reduction
Disulfide reduction
Bioreductive alkylation
Nitro reduction.

Each of the above described reactions and/or reaction steps can be used individually or in combination in a method to prepare a NEP-inhibitor or a prodrug thereof, such as a NEP inhibitor or prodrug thereof comprising a γ-amino-δ-biphenyl-α-methylalkanoic acid, or acid ester, such as alkyl ester, backbone. In particular the NEP-inhibitor is N-(3-carboxy-1-oxopropyl)-(4S)-(p-phenylphenylmethyl)-4-amino-(2R)-methylbutanoic acid or a salt thereof or a prodrug thereof.

SECTION C: EXAMPLES

The following Examples serve to illustrate the invention without limiting the scope thereof, while they on the other hand represent preferred embodiments of the reaction steps, intermediates and/or the process of the present invention.

ABBREVIATIONS

δ chemical shift
μl microlitre
Ac acetyl
AcOH acetic acid
Bn benzyl
Boc tert-butoxycarbonyl
$BF_3 \cdot Et_2O$ boron trifluoride diethyl etherate
$Bu_4NOH$ tetra-n-butylammonium hydroxide
t-BuOK potassium tert-butoxide
$BOC_2O$ di-tert-butyl carbonate
$CO_2$ carbon dioxide
$CH_2O$ formaldehyde
DBU 1,8-diazabicyclo[5,4,0]undec-7-ene
DME 1,2-dimethoxyethane
DMPU 1,3-dimethyl-3,4,56-tetrahedrao-2(1H)-pyrimidinone
de diastereomeric excess
dr diastereomeric ratio
DMF=dmf N,N-dimethylformamide
DMSO dimethylsulfoxide
ee enantiomeric excess
ES electrospray
ESI electrospray ionisation
Et ethyl
EtOAc ethyl acetate
EtOH ethanol
h hour(s)
HNMR proton nuclear magnetic resonance
$HCl_{(aq)}$ hydrogen chloride aqueous solution
HMDS 1,1,1,3,3,3-hexamethyldisilazane
HPLC high performance liquid chromatography
iPr isopropyl
$iPr_2NEt$ N-ethyldiisopropylamine
iPrOAc isopropyl acetate
iPrOH isopropanol
IR infra red
$K_2CO_3$ potassium carbonate
L litre
LC-MS liquid chromatography-mass spectrometry
LiCl lithium chloride
LDA lithium diisopropylamide
LHMDS lithium bis(trimethylsilyl)amide
M molarity
MeONa sodium methoxide
$MgSO_4$ magnesium sulfate
m/e mass-to-charge ratio
Me methyl
MeOH methanol
mg milligram min minute(s)
ml millilitre
mmol(s) millimole(s)
mol(s) mole(s)
MS mass spectrometry
N₂ nitrogen
Na₂CO₃ sodium carbonate
Na₂SO₃ sodium sulfite
Na₂SO₄ sodium sulfate
NH₄Cl ammonium chloride
NH₄OAc ammonium acetate
nm nanometre
NMR nuclear magnetic resonance
Ph phenyl
Piv pivaloyl
Piv-Cl pivaloyl chloride
ppm parts per million
PPTS pyridinium p-toluenesulfonate
pyr pyridine
RT=rt room temperature
SFC supercritical fluid chromatography
TBAH tetra-n-butylammonium hydroxide
tBu tertiary-butyl
TFA trifluoroacetic acid
THF tetrahydrofuran
TLC thin layer chromatography
Tol toluene
$t_R$ retention time
Xyl xylene
[Ir(cod)₂]BARF Bis(cyclooctadiene)iridium(I) tetrakis(3,5-bis(trifluoromethyl)-phenyl)borate
[Rh(cod)₂]O₃SCF₃ Bis(1,5-cyclooctadiene)rhodium(I) trifluoromethanesulfonate
[Rh(nbd)₂]BF₄ Bis(norbornadiene)rhodium(I) tetrafluoroborate
[Ru(cod)(OOCCF₃)₂] (1,5-Cyclooctadiene)ditrifluoroacetatoruthenium(II)
[RuCl₂(p-cymene)]₂ Diiodo(p-cymene)ruthenium(II) dimer In quoting NMR data, the following abbreviations may be used: s, singlet; d, doublet; t, triplet; q, quartet; quint., quintet; m, multiplet.

EXAMPLE 1

(R)-5-Biphenyl-4-ylmethyl-3-methyl-2-oxo-2,5-dihydro-pyrrole-1-carboxylic acid tert-butyl ester
(4a, R1=Boc)

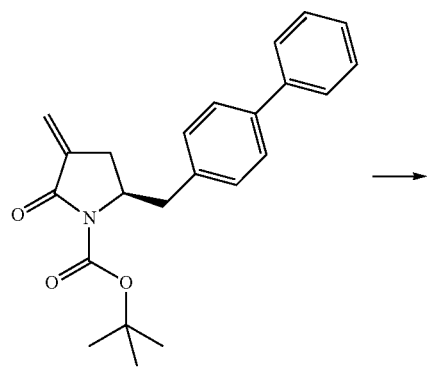

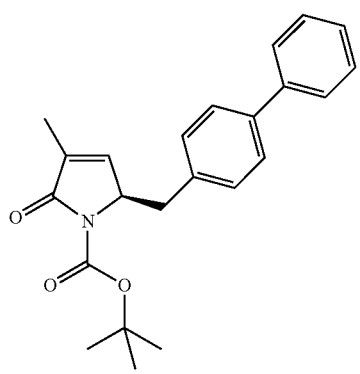

The mixture of (R)-5-Biphenyl-4-ylmethyl-3-methylene-2-oxo-pyrrolidine-1-carboxylic acid tert-butylester (1a, R1=Boc) (0.36 g, 1 mmol), Pd(PPh₃)₄ (70 mg, 0.06 mmol), PPh₃(31.5 mg, 0.12 mmol) and sodium hydrogencarbonate (0.27 g, 3.2 mmol) in 10 mL xylene is heated to reflux, and stirred overnight to give (R)-5-biphenyl-4-ylmethyl-3-methyl-2-oxo-2,5-dihydro-pyrrole-1-carboxylic acid tert-butyl ester (4a, R1=Boc) as determined by HPLC analysis. Spectroscopic data as for Example 2.

HPLC method: Column: Eclipse XDB-C18; 150×4.6 mm; 5 μm. Mobile Phase A (0.1% H₃PO₄) in water; Mobile Phase B (Acetonitrile). Gradient: 0 min (30% B); 8 min (95% B); 15 min (95% B). Flow rate: 1.00 ml min-1. Wavelength: 210 nm. Temperature: 30° C.

Retention time: 9.580 min

EXAMPLE 2

(R)-5-Biphenyl-4-ylmethyl-3-methyl-2-oxo-2,5-dihydro-pyrrole-1-carboxylic acid tert-butyl ester
(4a, R1=Boc)

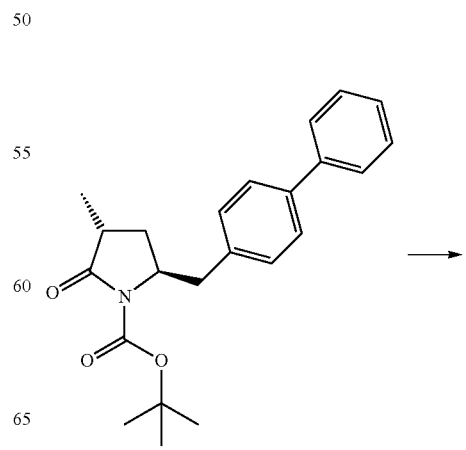

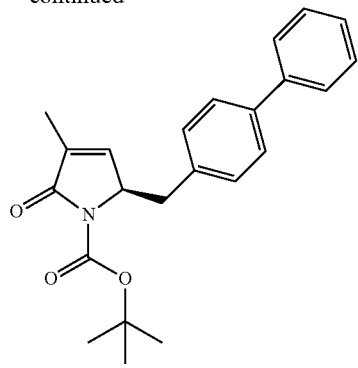

3.65 g (3R,5S)-5-Biphenyl-4-ylmethyl-3-methyl-2-oxo-pyrrolidine-1-carboxylic acid tert-butyl ester (3-a, R1=Boc) is added to toluene (20 ml). Sodium hydride (400 mg) is added to the mixture. The mixture is cooled to −15° C. 22 ml Potassium bis(trimethylsilyl)amide (0.5 M solution in toluene) is then added. The resulting mixture is then stirred for 1 h at −15° C. Phenylselenyl bromide (2.8 g) in toluene (20 ml) is then added to the mixture. The resulting mixture is stirred for 0.5 h at −15° C. The mixture is then poured into water and the phases are separated. The organic phase is concentrated under reduced pressure. Ethyl acetate (50 ml) and aqueous hydrogen peroxide (10 ml, 30%) is then added to the residue at ambient temperature. After 1 h of stirring, the phases are separated. The organic phase is washed with saturated sodium hydrogen carbonate solution, and then saturated sodium hydrogen sulfite solution, before being concentrated under reduced pressure. The residue is crystallised from isopropyl acetate/heptane (20 ml:5 ml) to afford (R)-5-biphenyl-4-ylmethyl-3-methyl-2-oxo-2,5-dihydro-pyrrole-1-carboxylic acid tert-butyl ester (4a, R1=Boc). 1H NMR (DMSO): 1.56 (9H), 1.66 (3H), 3.02 (1H), 3.32 (1H), 4.75 (1H), 7.04 (1H), 7.18 (2H), 7.36 (1H), 7.46 (2H), 7.60 (2H), 7.66 (2H).

(R)-5-Biphenyl-4-ylmethyl-3-methyl-2-oxo-2,5-dihydro-pyrrole-1-carboxylic acid tert-butyl ester (4a, R1=Boc) is a crystalline solid and can be characterised by single crystal X-ray analysis and X-ray powder patterns. The most intensive reflections in the X-ray diffraction pattern show the following interlattice plane intervals (average 2θ in [°] are indicated with error limit of ±0.2): 2θ in [°]: 7.7, 6.3, 5.1, 4.6, 4.1, 3.3, 3.1, 2.9. Data taken using a Bruker D8 Advance diffractometer using Cu—Kα radiation.

The X-ray Structure of the obtained crystals is shown in FIG. 1. Single crystal for this determination is obtained from acetone as solvent.

| Crystal data [recorded at 100(2) K] | |
|---|---|
| Empirical formula | $C_{23}H_{25}NO_3$ |
| Formula weight | 363.44 |
| Crystal system | Triclinic |
| Space group | P1 |
| Cell parameters | a = 6.501 (3) Å |
| | b = 8.372(4) Å |
| | c = 18.693(10) Å |
| | α = 93.333(19)° |
| | β = 95.36(2)° |
| | γ = 90.97(2)° |
| Volume of unit cell | 1011.0(9) Å³ |
| Z* | 2 |
| Calculated density | 1.194 mg m⁻³ |

*(number of asymmetric units in the unit cell)

EXAMPLE 3

(Z)—(R)-5-Biphenyl-4-yl-4-tert-butoxycarbonylamino-2-methylpent-2-enoic acid (5a, R1=Boc, R2=H, R3=CO₂H)

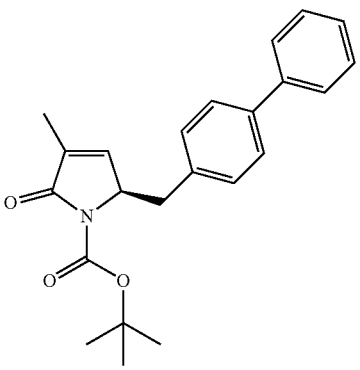

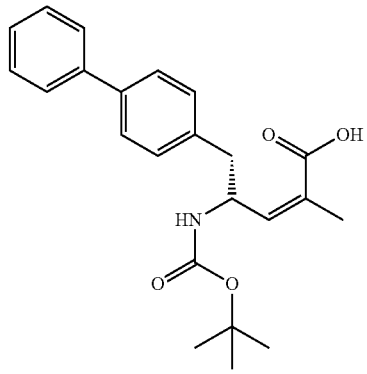

2.7 g (R)-5-Biphenyl-4-ylmethyl-3-methyl-2-oxo-2,5-dihydro-pyrrole-1-carboxylic acid tert-butyl ester (4-a, R1=Boc) is added to tetrahydrofuran (20 ml). Aqueous lithium hydroxide solution (10 ml, 3 M) is added and the mixture is stirred for 20 h at ambient temperature. The mixture is acidified by addition of phosphoric acid and subsequently diluted by addition of ethyl acetate. The phases are separated and the organic phase is washed with water and then concentrated under reduced pressure. Isopropyl acetate is added to the residue and the mixture is filtered to afford (Z)—(R)-5-Biphenyl-4-yl-4-tert-butoxycarbonylamino-2-methylpent-2-enoic acid (5a, R1=Boc, R2=H, R3=CO₂H). 1H NMR (DMSO): 1.28 (9H), 1.85 (3H), 2.78 (2H), 5.07 (1H), 5.92 (1H), 6.96 (1H), 7.30 (2H), 7.35 (1H), 7.46 (2H), 7.56 (2H), 7.63 (2H), 12.65 (1H).

(Z)—(R)-5-Biphenyl-4-yl-4-tert-butoxycarbonylamino-2-methylpent-2-enoic acid (5a, R1=Boc, R2=H, R3=CO₂H) is a crystalline solid and can be characterised an X-ray powder pattern. The most intensive reflections in the X-ray diffraction pattern show the following interlattice plane intervals (average 2θ in [°] are indicated with error limit of ±0.2): 2θ in [°]: 13.9, 10.5, 7.7, 6.9, 5.2, 5.0, 4.7, 4.6, 3.8. Data taken using a Bruker D8 Advance diffractometer using Cu—Kα radiation.

EXAMPLE 4

(3R,5S)-5-Biphenyl-4-ylmethyl-3-methyl-2-oxo-pyrrolidine-1-carboxylic acid tert-butyl ester (3a, R1=Boc) and (3S,5S)-5-biphenyl-4-ylmethyl-3-methyl-2-oxo-pyrrolidine-1-carboxylic acid tert-butyl ester (3b, R1=Boc)

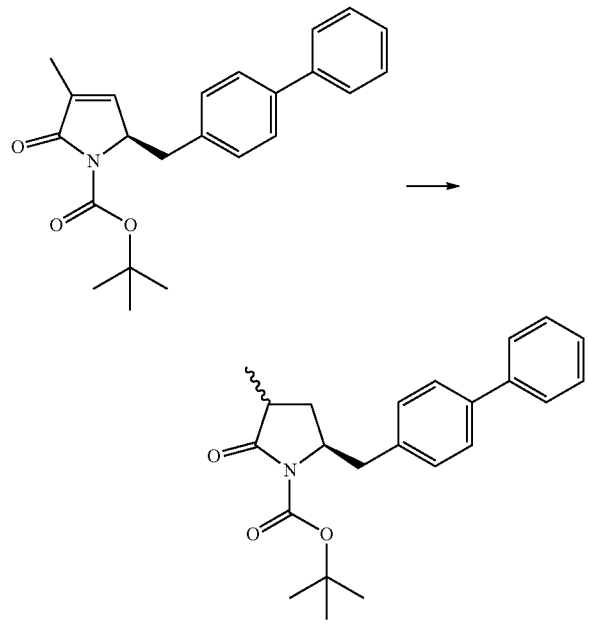

General Procedure 1

The Organometallic Complex (A) and Chiral Ligand (L) are added to a mixture of ethanol (0.041 ml) and dichloroethane (0.135 ml). The mixture is stirred for 0.5 h. The solvent is then removed under reduced pressure. (R)-5-Biphenyl-4-ylmethyl-3-methyl-2-oxo-2,5-dihydro-pyrrole-1-carboxylic acid tert-butyl ester (4a, R1=Boc) in a Solvent (S) (0.06 ml, identity of solvent given in the Table of Example 4) is added to the vessel containing the Organometallic Complex (A) and Chiral Ligand (L). Further solvent (identity given in the Table of Example 4) is added to give a final concentration of 4a (R1=Boc) of 84 mM. The ratio of 4a (R1=Boc) to Organometallic Complex (S/C ratio) is 25. The ratio of Chiral Ligand per atom of metal within the Organometallic Complex is 1.2.

Hydrogen gas at a pressure of 80 bar is then applied to the vessel containing the mixture. The mixture is then stirred under 80 bar hydrogen pressure for 16 h at ambient temperature.

The crude reaction solutions are analysed by HPLC to determine the ratio of (3R,5S)-5-biphenyl-4-ylmethyl-3-methyl-2-oxo-pyrrolidine-1-carboxylic acid tert-butyl ester (3a, R1=Boc) to (3S,5S)-5-biphenyl-4-ylmethyl-3-methyl-2-oxo-pyrrolidine-1-carboxylic acid tert-butyl ester (3b, R1=Boc).

General Procedure 2

(R)-5-Biphenyl-4-ylmethyl-3-methyl-2-oxo-2,5-dihydro-pyrrole-1-carboxylic acid tert-butyl ester (4a, R1=Boc) in a Solvent (S) (0.244 ml, identity of solvent given in the Table of Example 4) is added to the vessel containing the Organometallic Catalyst (C). Further solvent (identity given in the Table of Example 4) is added to give a final concentration of 4a (R1=Boc) of 84 mM. The ratio of 4a (R1=Boc) to Organometallic Complex (S/C ratio) is 25.

Hydrogen gas at a pressure of 80 bar is then applied to the vessel containing the mixture. The mixture is then stirred under 80 bar hydrogen pressure for 16 h at ambient temperature.

The crude reaction solutions are analysed by SFC to determine the ratio of (3R,5S)-5-biphenyl-4-ylmethyl-3-methyl-2-oxo-pyrrolidine-1-carboxylic acid tert-butyl ester (3a, R1=Boc) to (3S,5S)-5-biphenyl-4-ylmethyl-3-methyl-2-oxo-pyrrolidine-1-carboxylic acid test-butyl ester (3b, R1=Boc).

SFC Method (Example 4)

Column: Daicel Chiralpak AD-H; 250×4.6 mm. Mobile Phase A: Isopropyl acetate; Mobile Phase B: supercritical $CO_2$. Gradient: 0 min (20% A), 10 min (20% A), 10.5 min (40% A), 15.5 min (40% A), 16 min (20% A), 18 min (20% A). Flow rate: 1.5 ml $min^{-1}$. Wavelength: 210 nm.

Retention Times:
4 (R1=Boc): 6.8 min
3a (R1=Boc): 8.4 min
3b (R1=Boc): 7.9 min

Table of Example 4

| Method | General Procedure | Transition Metal Catalyst | | | | Diastereoselectivity | |
| | | Organometallic Catalyst (C) | Organometallic Complex (A) | Chiral Ligand (L) | Solvent (S) | 3a (R1 = Boc) (area % hplc) | 3b (R1 = Boc) (area % hplc) |
|---|---|---|---|---|---|---|---|
| 1 | 2 | — | — | — | S-2 | 12.2 | 87.8 |
| 2 | 1 | — | A-5 | L-3 | S-2 | 11 | 89 |
| 3 | 1 | — | A-3 | L-7 | S-2 | 4.7 | 95.3 |
| 4 | 1 | — | A-5 | L-14 | S-2 | 16.8 | 83.2 |
| 5 | 1 | — | A-4 | L-10 | S-3 | 3.5 | 96.5 |
| 6 | 1 | — | A-5 | L-6 | S-2 | 6.2 | 93.8 |
| 7 | 1 | — | A-2 | L-14 | S-3 | 39.3 | 60.7 |
| 8 | 1 | — | A-3 | L-17 | S-2 | 11.7 | 88.3 |
| 9 | 1 | — | A-3 | L-15 | S-2 | 9.7 | 90.3 |
| 10 | 2 | C-3 | — | — | S-2 | 7.2 | 92.8 |
| 11 | 1 | — | A-3 | L-16 | S-2 | 10.5 | 89.5 |
| 12 | 1 | — | A-2 | L-3 | S-3 | 19.1 | 80.9 |
| 13 | 1 | — | A-3 | L-18 | S-2 | 18.4 | 81.6 |
| 14 | 1 | — | A-3 | L-3 | S-2 | 8.2 | 91.8 |
| 15 | 1 | — | A-4 | L-13 | S-3 | 3.7 | 96.3 |
| 16 | 1 | — | A-2 | L-15 | S-3 | 6.9 | 93.1 |
| 17 | 1 | — | A-4 | L-9 | S-3 | 13.9 | 86.1 |

Table of Example 4

| Method | General Procedure | Transition Metal Catalyst Organometallic Catalyst (C) | Organometallic Complex (A) | Chiral Ligand (L) | Solvent (S) | Diastereoselectivity 3a (R1 = Boc) (area % hplc) | 3b (R1 = Boc) (area % hplc) |
|---|---|---|---|---|---|---|---|
| 18 | 1 | — | A-4 | L-6 | S-3 | 2.5 | 97.5 |
| 19 | 2 | C-2 | — | — | S-2 | 8.6 | 91.4 |
| 20 | 1 | — | A-5 | L-11 | S-2 | 7.1 | 92.9 |
| 21 | 1 | — | A-2 | L-13 | S-3 | 23.9 | 76.1 |
| 22 | 1 | — | A-3 | L-14 | S-2 | 43.1 | 56.9 |
| 23 | 1 | — | A-4 | L-12 | S-3 | 11.7 | 88.3 |
| 24 | 1 | — | A-4 | L-1 | S-3 | 7.8 | 92.2 |
| 25 | 2 | C-2 | — | — | S-3 | 9 | 91 |
| 26 | 2 | C-3 | — | — | S-3 | 7.3 | 92.7 |
| 27 | 2 | C-4 | — | — | S-3 | 5.3 | 94.7 |
| 28 | 1 | — | A-3 | L-13 | S-2 | 17.4 | 82.6 |
| 29 | 2 | C-4 | — | — | S-1 | 6.2 | 93.8 |
| 30 | 1 | — | A-3 | L-12 | S-2 | 52.3 | 47.7 |
| 31 | 1 | — | A-2 | L-12 | S-3 | 50.1 | 49.9 |
| 32 | 1 | — | A-4 | L-4 | S-3 | 20.3 | 79.7 |
| 33 | 1 | — | A-2 | L-6 | S-3 | 10.3 | 89.7 |
| 34 | 1 | — | A-4 | L-2 | S-3 | 10.8 | 89.2 |
| 35 | 1 | — | A-2 | L-8 | S-3 | 8.1 | 91.9 |
| 36 | 2 | C-1 | — | — | S-3 | 9.6 | 90.4 |
| 37 | 1 | — | A-4 | L-5 | S-3 | 12.3 | 87.7 |
| 38 | 1 | — | A-4 | L-8 | S-3 | 22.7 | 77.3 |
| 39 | 1 | — | A-1 | L-15 | S-1 | 18.8 | 81.2 |
| 40 | 1 | — | A-4 | L-11 | S-3 | 13.8 | 86.2 |
| 41 | 1 | — | A-3 | L-6 | S-2 | 12.3 | 87.7 |

For the purpose of Example 4, the following abbreviations apply:

Organometallic Catalyst (C)
C-1=[Rh(cod)(SL-P104-2)]O₃SCF₃=[Rh(cod)(L-19)]O₃SCF₃
C-2=[Rh(cod)(SL-P102-1)]BF₄=[Rh(cod)(L-20)]BF₄
C-3=[Rh(cod)(SL-P005-2)]BF₄=[Rh(cod)(L-21)]BF₄
C-4=[Ir(cod)((S,S)-UbaPHOX))]BARF=[Ir(cod)(L-22)]BARF Organometallic Complex (A)
A-1=[Ir(cod)₂]BARF
A-2=[Rh(cod)₂]O₃SCF₃
A-3=[Rh(nbd)₂]BF₄
A-4=[Ru(cod)(OOCCF₃)₂]
A-5=[RuCl₂(p-cymene)]₂

Chiral Ligand (L)
L-1=Atropisonner SL-A101-1
L-2=Atropisomer SL-A101-2
L-3=Atropisomer SL-A109-2
L-4=Atropisomer SL-A153-1
L-5=(S)-BINAP
L-6=(R)-PhanePhos
L-7=(R,R,R)-SpiroP
L-8=Josiphos SL-J002-2
L-9=Josiphos SL-J005-1
L-10=Josiphos SL-J302-1
L-11=Josiphos SL-J505-1
L-12=Mandyphos SL-M004-1
L-13=Mandyphos SL-M004-2
L-14=Taniaphos SL-T001-1
L-15=Taniaphos SL-T002-1
L-16=Walphos SL-W001-1
L-17=Walphos SL-W008-1
L-18=Walphos SL-W008-2
L-19=Phospholane SL-P104-2
L-20=Phospholane SL-P102-1
L-21=Phospholane SL-P005-2
L-22=(S,S)-UbaPHOX Solvent (S)
S-1=Dichloroethane/Tetrahydrofuran (7:1)
S-2=Ethanol/Tetrahydrofuran (7:1)
S-3=Tetrahydrofuran

EXAMPLE 5

(3R,5S)-5-Biphenyl-4-ylmethyl-3-methyl-2-oxo-pyrrolidine-1-carboxylic acid tert-butyl ester (3a, R1=Boc) and (3S,5S)-5-biphenyl-4-ylmethyl-3-methyl-2-oxo-pyrrolidine-1-carboxylic acid tert-butyl ester (3b, R1=Boc)

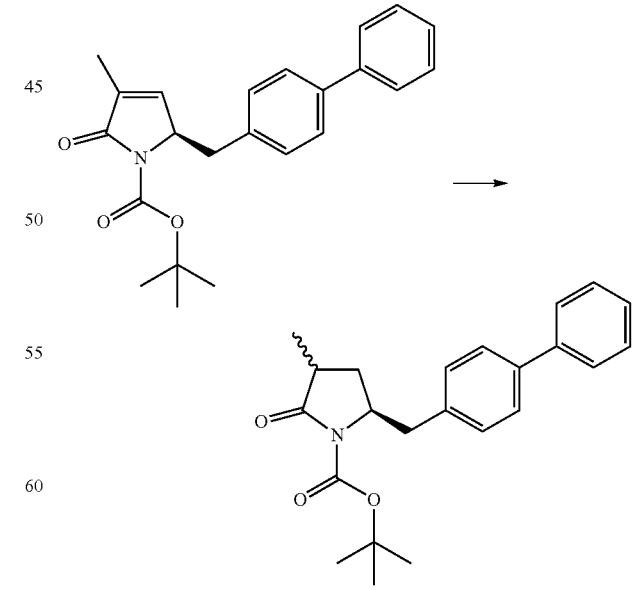

General Procedure (Methods 1-6)

50 mg (R)-5-Biphenyl-4-ylmethyl-3-methyl-2-oxo-2,5-dihydro-pyrrole-1-carboxylic acid tert-butyl ester (4a, R1=Boc) is added to a solvent (1 ml) at ambient temperature. The heterogeneous catalyst (10 mg) is added to the mixture. Hydrogen gas is applied to the mixture. The mixture is stirred overnight at ambient temperature and pressure.

The crude reaction solutions are analysed by HPLC to determine the ratio of (3R,5S)-5-biphenyl-4-ylmethyl-3-methyl-2-oxo-pyrrolidine-1-carboxylic acid tert-butyl ester (3a, R1=Boc) to (3S,5S)-5-biphenyl-4-ylmethyl-3-methyl-2-oxo-pyrrolidine-1-carboxylic acid tert-butyl ester (3b, R1=Boc).

Method 1
Solvent: Ethanol; Heterogeneous Catalyst: Palladium on Carbon (10% loading, 50% water wet). Ratio (3a:3b):17:83
Method 2
Solvent: Isopropyl acetate; Heterogeneous Catalyst: Palladium on Carbon (10% loading, 50% water wet). Ratio (3a:3b):4:96
Method 3
Solvent: Ethanol; Heterogeneous Catalyst: Rhodium on Carbon (5% loading). Ratio (3a:3b):>1:99
Method 4
Solvent: Isopropyl acetate; Heterogeneous Catalyst: Rhodium on Carbon (5% loading). Ratio (3a:3-b):>1:99
Method 5
Solvent: Ethanol; Heterogeneous Catalyst: Platinum on Carbon (10% loading). Ratio (3a:3b):8:92
Method 6
Solvent: Isopropyl acetate; Heterogeneous Catalyst: Platinum on Carbon (10% loading). Ratio (3a:3-b):7:93

HPLC Method 1 (Example 5, Methods 1-6)
Column: AD-RH Chiralpak; 150×4.6 mm. Mobile Phase A (water); Mobile Phase B (Acetonitrile). Isocratic: 0 min (20% B); 15 min (20% B). Flow rate: 0.5 ml min$^{-1}$.
Wavelength 210 nm. Column temperature: 40° C.
Retention Times:
(3a, R1=Boc): 6.8 min
(3b, R1=Boc): 7.5 min HPLC Method 2 (Example 5, Methods 1-6)
Column: Zorbax SB-C18; 150×3.0 mm; 3.5 µm. Mobile Phase A (0.01 M KH$_2$PO$_4$ in water); Mobile Phase B (Acetonitrile). Gradient: 0 min (30% B); 10 min (80% B); 15 min (80% B); 15.1 min (30% B); 18 min (30% B). Flow rate: 1.0 ml min$^{-1}$. Wavelength: 210 nm. Temperature 50° C.
Retention Times:
(4a, R1=Boc): 9.5 min
(1a, R1=Boc): 9.7 min
(3a, R1=Boc; 3-b, R1=Boc): 9.9 min

EXAMPLE 6

(2R,4S)-5-Biphenyl-4-yl-4-tert-butoxycarbonylamino-2-methylpentanoic acid (2a, R1=Boc, R2=H, R3=CO$_2$H) or (2S,4S)-5-Biphenyl-4-yl-4-tert-butoxycarbonylamino-2-methylpentanoic acid (2b, R1=Boc, R2=H, R3 =CO$_2$H)

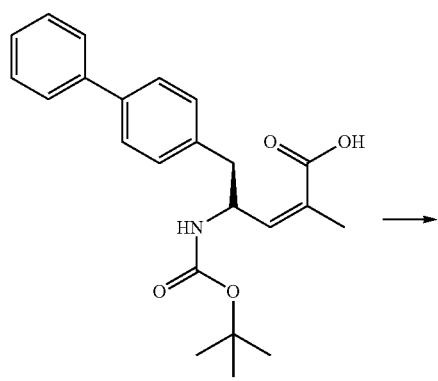

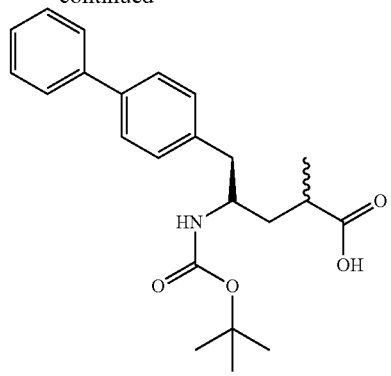

1 g (Z)—(R)-5-Biphenyl-4-yl-4-tert-butoxycarbonylamino-2-methylpent-2-enoic acid (5a, R1=Boc, R2=H, R3=CO$_2$H) is added to isopropyl acetate (10 ml) at ambient temperature. Triethylamine (0.37 ml) is then added to the mixture. The heterogeneous catalyst (100 mg or 200 mg) is added to the mixture. Hydrogen gas at ambient pressure is applied to the mixture. The mixture is stirred overnight at ambient temperature and pressure.

The crude reaction solution is analysed by HPLC to determine the ratio of (2R,4S)-5-biphenyl-4-yl-4-tert-butoxycarbonylamino-2-methylpentanoic acid (2a, R1=Boc, R2=H, R3=CO$_2$H) to (2S,4S)-5-biphenyl-4-yl-4-tert-butoxycarbonylamino-2-methylpentanoic acid (2b, R1=Boc, R2=H, R3=CO$_2$H).

Method 1
Heterogeneous Catalyst: Palladium on Carbon (10% loading, 50% water wet); 100 mg. Ratio (2a:2b):54:46.
Method 2
Heterogeneous Catalyst: Platinum on Carbon (10% loading); 100 mg. Ratio (2a:2b):42:58.
Method 3
Heterogeneous Catalyst: Rhodium on Carbon (5% loading); 200 mg. Ratio (2a:2b):55:45.

HPLC Method (Example 6)
Column: Daicel Chiralpak QN-AX; 150×4.6 mm; 5 µm. Mobile Phase A: Methanol/EtOH (1:1), 0.1% AcOH (v/v), 0.01% NH$_4$OAc (m/v). Isocratic: 0 min (100% A); 20 min (100% A). Flow rate 0.5 ml min$^{-1}$. Wavelength: 254 nm.
Retention Times:
(2a, R1=Boc, R2=H, R3=CO$_2$H): 7.6 min
(2b, R1=Boc, R2=H, R3=CO$_2$H): 10.3 min

EXAMPLE 7

(2R,4S)-5-Biphenyl-4-yl-4-tert-butoxycarbonylamino-2-methylpentanoic acid (2a, R1=Boc, R2=H, R3=CO$_2$H) or (2S,4S)-5-Biphenyl-4-yl-4-tert-butoxycarbonylamino-2-methylpentanoic acid (2b, R1=Boc, R2=H, R3 =CO$_2$H)

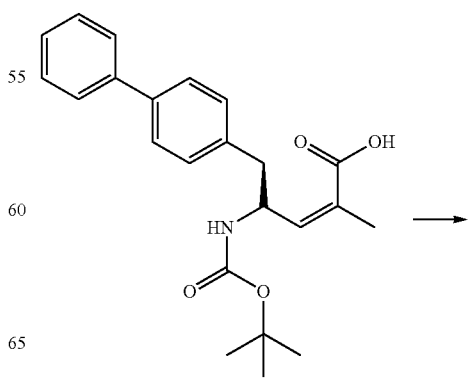

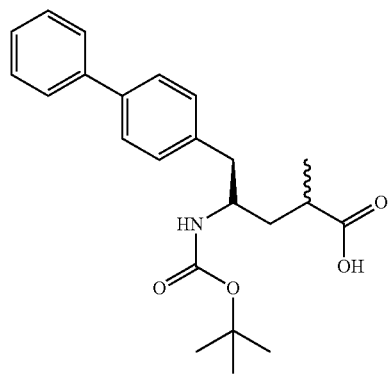

General Procedure 1

The Organometallic Complex (A) and Chiral Ligand (L) are added to a mixture of ethanol (0.041 ml) and dichloroethane (0.135 ml). The mixture is stirred for 0.5 h. The solvent is then removed under reduced pressure. (Z)—(R)-5-Biphenyl-4-yl-4-tert-butoxycarbonylamino-2-methylpent-2-enoic acid (5a, R1=Boc, R2=H, R3=CO$_2$H) in a Solvent (S) (0.244 ml, identity of solvent given in the Table of Example 7) is added to the vessel containing the Organometallic Complex (A) and Chiral Ligand (L). Further solvent (identity given in the Table of Example 7) is added to give a final concentration of 5a (R1=Boc, R2=H, R3=CO$_2$H) as given in the Table of Example 7. The ratio of 5a (R1=Boc, R2=H, R3=CO$_2$H) to Organometallic Complex (S/C ratio) is given in the Table of Example 7. The ratio of Chiral Ligand per atom of metal within the Organometallic Complex is given in the Table of Example 7.

Hydrogen gas at a pressure of 20 bar is then applied to the vessel containing the mixture. The mixture is then stirred under 20 bar hydrogen pressure for 16 h at a temperature of 40° C.

The crude reaction solutions are analysed by HPLC to determine the ratio of (2R,4S)-5-biphenyl-4-yl-4-tert-butoxycarbonylamino-2-methylpentanoic acid (2a, R1=Boc, R2=H, R3=CO$_2$H) to (2S,4S)-5-biphenyl-4-yl-4-tert-butoxycarbonylamino-2-methylpentanoic acid (2b, R1=Boc, R2=H, R3=CO$_2$H)

General Procedure 2

(Z)—(R)-5-Biphenyl-4-yl-4-tert-butoxycarbonylamino-2-methylpent-2-enoic acid (5a, R1=Boc, R2=H, R3=CO$_2$H) in a Solvent (S) (0.244 ml, identity of solvent given in the Table of Example 7) is added to the vessel containing the Organometallic Catalyst (C). Further solvent (identity given in the Table of Example 7) is added to give a final concentration of 5a (R1=Boc, R2=H, R3=CO$_2$H) as given in the Table of Example 7. The ratio of 5a (R1=Boc, R2=H, R3=CO$_2$H) to Organometallic Complex (S/C ratio) is given in the Table of Example 7.

Hydrogen gas at a pressure of 20 bar is then applied to the vessel containing the mixture. The mixture is then stirred under 20 bar hydrogen pressure for 16 h at a temperature of 40° C.

The crude reaction solutions are analysed by HPLC to determine the ratio of (2R,4S)-5-biphenyl-4-yl-4-tert-butoxycarbonylamino-2-methylpentanoic acid (2a, R1=Boc, R2=H, R3=CO$_2$H) to (2S,4S)-5-biphenyl-4-yl-4-tert-butoxycarbonylamino-2-methylpentanoic acid (2b, R1=Boc, R2=H, R3=CO$_2$H)

General Procedure 3

Solvent (S) (volume and identity of solvent given in the Table of Example 7) is added to a mixture of the Organometallic Complex (A) and the Chiral Ligand (L) in Vessel A. The mixture is stirred for 30 min at a temperature of 55° C.

Solvent (S) (volume and identity of solvent given in the Table of Example 7) is added to (Z)—(R)-5-biphenyl-4-yl-4-tert-butoxycarbonylamino-2-methylpent-2-enoic acid (5a, R1=Boc, R2=H, R3=CO$_2$H) in Vessel B.

The contents of Vessel A and Vessel B are transferred to Vessel C (empty). The final concentration of 5a (R1=Boc, R2=H, R3=CO$_2$H) is given in the Table of Example 7. The S/C ratio is given in the Table of Example 7. The ratio of Chiral Ligand per atom of metal within the Organometallic Complex is given in the Table of Example 7.

Hydrogen gas is then applied to Vessel C (temperature, time and pressure is given in the Table of Example 7).

The crude reaction solutions are analysed by HPLC to determine the ratio of (2R,4S)-5-biphenyl-4-yl-4-tert-butoxycarbonylamino-2-methylpentanoic acid (2a, R1=Boc, R2=H, R3=CO$_2$H) to (2S,4S)-5-biphenyl-4-yl-4-tert-butoxycarbonylamino-2-methylpentanoic acid (2b, R1=Boc, R2=H, R3=CO$_2$H).

HPLC Method (Example 7)

Column: Daicel Chiralpak QD-AX; 150×4.6 mm; 5 μm. Mobile Phase A: Methanol/EtOH (1:1), 0.1% AcOH (v/v), 0.01% NH$_4$OAc (m/v). Isocratic: 0 min (100% A); 20 min (100% A). Flow rate 0.5 ml min$^{-1}$. Wavelength: 254 nm.
Retention Times:
(2a, R1=Boc, R2=H, R3=CO$_2$H): 7.7 min
(2b, R1=Boc, R2=H, R3=CO$_2$H): 10.6 min
(5a, R1=Boc, R2=H, R3=CO$_2$H): 10.8 min Table of Example 7

| Method | General Procedure | Transition Metal Catalyst Organometallic Catalyst (C) | Organometallic Complex (A) | Chiral Ligand (L) | Ratio of Ligand per atom of metal within the Organometallic Complex | Ratio of 5a (R1 = Boc, R2 = H, R3 = CO₂H) to Transition Metal Catalyst (S/C ratio) | Amount of 5a (R1 = Boc, R2 = H, R3 = CO₂H) (mmol) | Solvent (S) | ml of Solvent (5a, R1 = Boc, R2 = H, R3 = CO₂H) | Solvent Volume (Transition Metal Catalyst) (ml) | Solvent Volume (Total reaction volume) (ml) | Concentration of 5a (R1 = Boc, R2 = H, R3 = CO₂H) (mM) |
|---|---|---|---|---|---|---|---|---|---|---|---|---|
| 1  | 1 | — | A-3 | L-7  | 1.20 | 25  | 0.042 | S-2 | — | — | 0.5 | 84 |
| 2  | 1 | — | A-3 | L-24 | 1.20 | 25  | 0.042 | S-3 | — | — | 0.5 | 84 |
| 3  | 1 | — | A-3 | L-9  | 1.20 | 25  | 0.042 | S-3 | — | — | 0.5 | 84 |
| 4  | 1 | — | A-3 | L-1  | 1.20 | 25  | 0.042 | S-3 | — | — | 0.5 | 84 |
| 5  | 1 | — | A-2 | L-22 | 1.20 | 25  | 0.042 | S-2 | — | — | 0.5 | 84 |
| 6  | 1 | — | A-3 | L-30 | 1.20 | 25  | 0.042 | S-2 | — | — | 0.5 | 84 |
| 7  | 1 | — | A-3 | L-21 | 1.20 | 25  | 0.042 | S-2 | — | — | 0.5 | 84 |
| 8  | 1 | — | A-2 | L-21 | 1.20 | 25  | 0.042 | S-2 | — | — | 0.5 | 84 |
| 9  | 1 | — | A-2 | L-5  | 1.20 | 25  | 0.042 | S-2 | — | — | 0.5 | 84 |
| 10 | 1 | — | A-1 | L-10 | 1.20 | 25  | 0.042 | S-3 | — | — | 0.5 | 84 |
| 11 | 1 | — | A-2 | L-13 | 1.20 | 25  | 0.042 | S-3 | — | — | 0.5 | 33 |
| 12 | 3 | — | A-2 | L-3  | 1.05 | 100 | 0.5   | S-3 | 10 | 5 | 15 | 84 |
| 13 | 1 | — | A-2 | L-28 | 1.20 | 25  | 0.042 | S-2 | — | — | 0.5 | 84 |
| 14 | 1 | — | A-1 | L-18 | 1.20 | 25  | 0.042 | S-3 | — | — | 0.5 | 84 |
| 15 | 1 | — | A-3 | L-30 | 1.20 | 25  | 0.042 | S-3 | — | — | 0.5 | 84 |
| 16 | 1 | — | A-3 | L-10 | 1.20 | 25  | 0.042 | S-3 | — | — | 0.5 | 84 |
| 17 | 1 | — | A-2 | L-2  | 1.20 | 25  | 0.042 | S-2 | — | — | 0.5 | 84 |
| 18 | 1 | — | A-1 | L-17 | 1.20 | 25  | 0.042 | S-2 | — | — | 0.5 | 84 |
| 19 | 1 | — | A-2 | L-14 | 1.20 | 25  | 0.042 | S-2 | — | — | 0.5 | 84 |
| 20 | 1 | — | A-2 | L-27 | 1.20 | 25  | 0.042 | S-2 | — | — | 0.5 | 84 |
| 21 | 1 | — | A-2 | L-15 | 1.20 | 25  | 0.042 | S-2 | — | — | 0.5 | 84 |
| 22 | 1 | — | A-1 | L-8  | 1.20 | 25  | 0.042 | S-2 | — | — | 0.5 | 84 |
| 23 | 1 | — | —   | —    | —    | 25  | 0.042 | S-3 | — | — | 0.5 | 84 |
| 24 | 2 | C-2 | A-3 | L-20 | 1.20 | 25  | 0.042 | S-3 | — | — | 0.5 | 84 |
| 25 | 1 | — | A-3 | L-26 | 1.20 | 25  | 0.042 | S-2 | — | — | 0.5 | 84 |
| 26 | 1 | — | A-3 | L-11 | 1.20 | 25  | 0.042 | S-2 | — | — | 0.5 | 84 |
| 27 | 1 | — | A-3 | L-5  | 1.20 | 25  | 0.042 | S-3 | — | — | 0.5 | 84 |
| 28 | 1 | — | A-2 | L-13 | 1.20 | 25  | 0.042 | S-3 | — | — | 0.5 | 84 |
| 29 | 1 | — | A-2 | L-25 | 1.20 | 25  | 0.042 | S-2 | — | — | 0.5 | 84 |
| 30 | 1 | — | A-2 | L-6  | 1.20 | 25  | 0.042 | S-2 | — | — | 0.5 | 84 |
| 31 | 1 | — | A-2 | L-31 | 1.20 | 25  | 0.042 | S-2 | — | — | 0.5 | 84 |
| 32 | 1 | — | A-3 | L-20 | 1.20 | 25  | 0.042 | S-2 | — | — | 0.5 | 84 |
| 33 | 1 | — | A-3 | L-24 | 1.20 | 25  | 0.042 | S-3 | — | — | 0.5 | 84 |
| 34 | 1 | — | —   | —    | —    | 25  | 0.042 | S-2 | — | — | 0.5 | 84 |
| 35 | 2 | C-3 | —   | —    | —    | 25  | 0.042 | S-2 | — | — | 0.5 | 84 |
| 36 | 1 | — | A-2 | L-18 | 1.20 | 25  | 0.042 | S-2 | — | — | 0.5 | 84 |
| 37 | 1 | — | A-1 | L-15 | 1.20 | 25  | 0.042 | S-3 | — | — | 0.5 | 84 |
| 38 | 1 | — | A-1 | L-23 | 1.20 | 25  | 0.042 | S-3 | — | — | 0.5 | 84 |
| 39 | 1 | — | A-3 | L-26 | 1.20 | 25  | 0.042 | S-3 | — | — | 0.5 | 84 |

-continued

Table of Example 7

| Method | General Procedure | Transition Metal Catalyst Organo-metallic Catalyst (C) | Transition Metal Catalyst Organo-metallic Complex (A) | Chiral Ligand (L) | Ratio of Ligand per atom of metal within the Organometallic Complex | Ratio of 5a (R1 = Boc, R2 = H, R3 = CO2H) to Transition Metal Catalyst (S/C ratio) | Amount of 5a (R1 = Boc, R2 = H, R3 = CO2H) (mmol) | Solvent (S) | ml of Solvent (5a, R1 = Boc, R2 = H, R3 = CO2H) | Solvent Volume (Transition Metal Catalyst) (ml) | Solvent Volume (Total reaction volume) (ml) | Concentration of 5a (R1 = Boc, R2 = H, R3 = CO2H) (mM) |
|---|---|---|---|---|---|---|---|---|---|---|---|---|
| 40 | 1 | — | A-1 | L-29 | 1.20 | 25 | 0.042 | S-3 | — | — | 0.5 | 84 |
| 41 | 1 | — | A-2 | L-29 | 1.20 | 25 | 0.042 | S-3 | — | — | 0.5 | 84 |
| 42 | 1 | — | A-3 | L-11 | 1.20 | 25 | 0.042 | S-3 | — | — | 0.5 | 84 |
| 43 | 1 | — | A-3 | L-3 | 1.20 | 25 | 0.042 | S-2 | — | — | 0.5 | 84 |
| 44 | 1 | — | A-3 | L-27 | 1.20 | 25 | 0.042 | S-2 | — | — | 0.5 | 84 |
| 45 | 1 | — | A-2 | L-23 | 1.20 | 25 | 0.042 | S-2 | — | — | 0.5 | 84 |
| 46 | 1 | — | A-2 | L-17 | 1.20 | 25 | 0.042 | S-3 | — | — | 0.5 | 84 |
| 47 | 1 | — | A-3 | L-4 | 1.20 | 25 | 0.042 | S-2 | — | — | 0.5 | 84 |
| 48 | 1 | — | A-1 | L-17 | 1.20 | 25 | 0.042 | S-3 | — | — | 0.5 | 84 |
| 49 | 1 | — | A-3 | L-1 | 1.20 | 25 | 0.042 | S-2 | — | — | 0.5 | 84 |
| 50 | 1 | — | A-2 | L-25 | 1.20 | 25 | 0.042 | S-3 | — | — | 0.5 | 84 |
| 51 | 1 | — | A-3 | L-16 | 1.20 | 25 | 0.042 | S-2 | — | — | 0.5 | 84 |
| 52 | 1 | — | A-2 | L-26 | 1.20 | 25 | 0.042 | S-3 | — | — | 0.5 | 84 |
| 53 | 1 | — | A-2 | L-14 | 1.20 | 25 | 0.042 | S-2 | — | — | 0.5 | 84 |
| 54 | 1 | — | A-3 | L-12 | 1.20 | 25 | 0.042 | S-2 | — | — | 0.5 | 84 |
| 55 | 1 | — | A-2 | L-4 | 1.20 | 25 | 0.042 | S-3 | — | — | 0.5 | 84 |
| 56 | 1 | — | A-3 | L-29 | 1.20 | 25 | 0.042 | S-3 | — | — | 0.5 | 84 |
| 57 | 2 | C-1 | — | — | — | 25 | 0.042 | S-2 | — | — | 0.5 | 84 |
| 58 | 1 | — | A-3 | L-23 | 1.20 | 25 | 0.042 | S-2 | — | — | 0.5 | 84 |
| 59 | 1 | — | A-2 | L-19 | 1.20 | 25 | 0.042 | S-3 | — | — | 0.5 | 84 |
| 60 | 1 | — | A-1 | L-4 | 1.20 | 25 | 0.042 | S-2 | — | — | 0.5 | 84 |
| 61 | 1 | — | A-2 | L-11 | 1.20 | 25 | 0.042 | S-2 | — | — | 0.5 | 84 |
| 62 | 1 | — | A-3 | L-2 | 1.20 | 25 | 0.042 | S-2 | — | — | 0.5 | 84 |
| 63 | 1 | — | A-2 | L-14 | 1.20 | 25 | 0.042 | S-2 | — | — | 0.5 | 84 |
| 64 | 1 | — | A-3 | L-22 | 1.20 | 25 | 0.042 | S-3 | — | — | 0.5 | 84 |
| 65 | 1 | — | A-2 | L-5 | 1.20 | 25 | 0.042 | S-2 | — | — | 0.5 | 84 |
| 66 | 1 | — | A-3 | L-13 | 1.20 | 25 | 0.042 | S-2 | — | — | 0.5 | 84 |
| 67 | 1 | — | A-2 | L-19 | 1.20 | 25 | 0.042 | S-2 | — | — | 0.5 | 84 |
| 68 | 1 | — | A-2 | L-31 | 1.20 | 25 | 0.042 | S-3 | — | — | 0.5 | 84 |
| 69 | 1 | — | A-2 | L-9 | 1.20 | 25 | 0.042 | S-2 | — | — | 0.5 | 84 |
| 70 | 1 | — | A-3 | L-9 | 1.20 | 25 | 0.042 | S-2 | — | — | 0.5 | 84 |
| 71 | 1 | — | A-2 | L-30 | 1.20 | 25 | 0.042 | S-2 | — | — | 0.5 | 84 |
| 72 | 1 | — | A-1 | L-19 | 1.20 | 25 | 0.042 | S-3 | — | — | 0.5 | 84 |
| 73 | 1 | — | A-3 | L-15 | 1.20 | 25 | 0.042 | S-2 | — | — | 0.5 | 84 |
| 74 | 3 | — | A-2 | L-13 | 1.05 | 25 | 0.5 | S-3 | 10 | 5 | 15 | 33 |
| 75 | 3 | — | A-2 | L-13 | 1.05 | 25 | 0.5 | S-2 | 10 | 5 | 15 | 33 |
| 76 | 3 | — | A-3 | L-26 | 1.05 | 25 | 0.26 | S-1 | 10 | 5 | 15 | 17 |
| 77 | 1 | — | A-4 | L-6 | 1.20 | 25 | 0.042 | S-2 | — | — | 0.5 | 84 |
| 78 | 2 | C-2 | — | — | — | 25 | 0.042 | S-2 | — | — | 0.5 | 84 |

-continued

Table of Example 7

| Method | General Procedure | Transition Metal Catalyst Organometallic Catalyst (C) | Transition Metal Catalyst Organometallic Complex (A) | Chiral Ligand (L) | Ratio of Ligand per atom of metal within the Organometallic Complex | Ratio of 5a (R1 = Boc, R2 = H, R3 = CO$_2$H) to Transition Metal Catalyst (S/C ratio) | Amount of 5a (R1 = Boc, R2 = H, R3 = CO$_2$H) (mmol) | Solvent (S) | ml of Solvent (5a, R1 = Boc, R2 = H, R3 = CO$_2$H) | Solvent Volume (Transition Metal Catalyst) (ml) | Solvent Volume (Total reaction volume) (ml) | Concentration of 5a (R1 = Boc, R2 = H, R3 = CO$_2$H) (mM) |
|---|---|---|---|---|---|---|---|---|---|---|---|---|
| 79 | 1 | — | A-3 | L-3 | 1.20 | 25 | 0.042 | S-3 | — | — | 0.5 | 84 |
| 80 | 1 | — | A-3 | L-22 | 1.20 | 25 | 0.042 | S-2 | — | — | 0.5 | 84 |
| 81 | 1 | — | A-3 | L-12 | 1.20 | 25 | 0.042 | S-2 | — | — | 0.5 | 84 |
| 82 | 1 | — | A-2 | L-8 | 1.20 | 25 | 0.042 | S-2 | — | — | 0.5 | 84 |
| 83 | 1 | — | A-3 | L-8 | 1.20 | 25 | 0.042 | S-2 | — | — | 0.5 | 84 |
| 84 | 1 | — | A-2 | L-7 | 1.20 | 25 | 0.042 | S-2 | — | — | 0.5 | 84 |
| 85 | 1 | — | A-2 | L-25 | 1.20 | 25 | 0.042 | S-2 | — | — | 0.5 | 84 |
| 86 | 1 | — | A-3 | L-1 | 1.20 | 25 | 0.042 | S-2 | — | — | 0.5 | 84 |
| 87 | 1 | — | A-2 | L-7 | 1.20 | 25 | 0.042 | S-2 | — | — | 0.5 | 84 |
| 88 | 1 | — | A-2 | L-20 | 1.20 | 25 | 0.042 | S-2 | — | — | 0.5 | 84 |
| 89 | 2 | C-3 | — | — | — | 25 | 0.042 | S-3 | — | — | 0.5 | 84 |
| 90 | 3 | — | A-4 | L-25 | 1.05 | 25 | 0.26 | S-1 | 10 | 5 | 15 | 17 |
| 91 | 1 | — | A-2 | L-28 | 1.20 | 25 | 0.042 | S-2 | — | — | 0.5 | 84 |
| 92 | 1 | — | A-1 | L-16 | 1.20 | 25 | 0.042 | S-3 | — | — | 0.5 | 84 |
| 93 | 1 | — | A-3 | L-16 | 1.20 | 25 | 0.042 | S-2 | — | — | 0.5 | 84 |
| 94 | 2 | C-1 | — | — | — | 25 | 0.042 | S-2 | — | — | 0.5 | 84 |
| 95 | 1 | — | A-2 | L-10 | 1.20 | 25 | 0.042 | S-2 | — | — | 0.5 | 84 |
| 96 | 1 | — | A-3 | L-18 | 1.20 | 25 | 0.042 | S-2 | — | — | 0.5 | 84 |

For the purpose of Example 7, the following abbreviations apply:
Organometallic Catalyst (C)
C-1=[Rh(cod)(SL-P005-1)]BF$_4$=[Rh(cod)(L-32)]BF$_4$
C-2=[Rh(cod)(SL-P114-1)]BF$_4$=[Rh(cod)(L-33)]BF$_4$
C-3=[Rh(cod)(SL-P102-1)]O$_3$SCF$_3$=[Rh(cod)(L-34)]O$_3$SCF$_3$
Organometallic Complex (A)
A-1=[Rh(cod)$_2$]O$_3$SCF$_3$
A-2=[Rh(nbd)$_2$]BF$_4$
A-3=[Ru(cod)(OOCCF$_3$)$_2$]
A-4=[RuI$_2$(p-cymene)]$_2$
Chiral Ligand (L)
L-1=Atropisomer SL-A101-1
L-2=Atropisomer SL-A101-2
L-3=Atropisomer SL-A109-2
L-4=(R)-Xyl-BINAP
L-5=Atropisomer SL-A241-1
L-6=Atropisomer SL-A242-1
L-7=(R,R)-ChiraPhos
L-8=(R,R)-MOD-DIOP
L-9=(R,R)-BDPP
L-10=(R)-PhanePhos
L-11=(R)-SDP
L-12=Fenphos SL-F102-1
L-13=Fenphos SL-F356-1
L-14=Josiphos SL-J003-1
L-15=Josiphos SL-J005-2
L-16=Josiphos SL-J216-1
L-17=Josiphos SL-J226-2
L-18=Josiphos SL-J302-1
L-19=Josiphos SL-J504-1
L-20=Josiphos SL-J505-1
L-21=Josiphos SL-J505-2
L-22=Mandyphos SL-M001-1
L-23=Mandyphos SL-M002-2
L-24=Mandyphos SL-M003-1
L-25=Mandyphos SL-M004-1
L-26=Mandyphos SL-M004-2
L-27=Taniaphos SL-T001-1
L-28=Taniaphos SL-T002-1
L-29=Walphos SL-W001-1
L-30=Walphos SL-W008-1
L-31=Walphos SL-W008-2
L-32=Phospholane SL-P005-1
L-33=Phospholane SL-P114-1
L-34=Phospholane SL-P102-1
Solvent (S)
S-1=Ethanol
S-2=Ethanol/Tetrahydrofuran (2:1)
S-3=Tetrahydrofuran

EXAMPLE 8

(Z)—(R)-4-Amino-5-biphenyl-4-yl-2-methyl-pent-2-enoic acid hydrochloride (5a, R1=H, R2=H, R3=CO$_2$H)

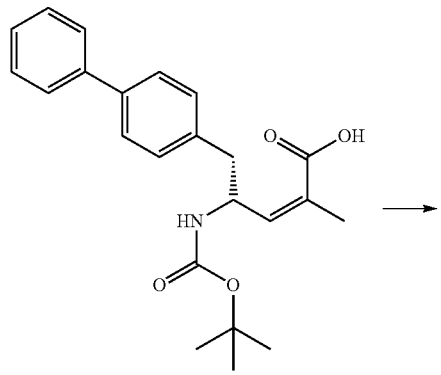

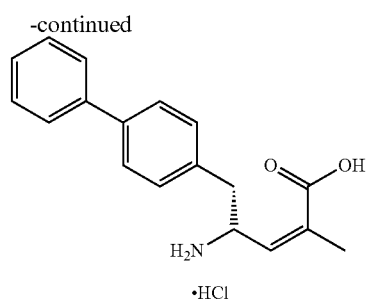

5 g (Z)—(R)-5-Biphenyl-4-yl-4-tert-butoxycarbonylamino-2-methylpent-2-enoic acid (5a, R1=Boc, R2=H, R3=CO$_2$H) is added to ethanol (50 ml) at room temperature. The mixture was stirred for 15 min and a further quantity of ethanol (10 ml) added. The mixture is then heated to 65° C. Thionyl chloride (1.44 ml) is added and the mixture stirred for 30 min. The volatiles are removed under reduced pressure. Heptane (50 ml) is added to the residue and the volatiles removed under reduced pressure. Ethyl acetate (30 ml) is added to the residue. The solid is collected by filtration. A portion of the solid (1 g) is suspended in ethyl acetate and stirred for 1 h at room temperature. The solid is collected by filtration and dried in vacuo to afford (Z)—(R)-4-amino-5-biphenyl-4-yl-2-methyl-pent-2-enoic acid hydrochloride (5a, R1=H, R2=H, R3=CO$_2$H). 1H-NMR (DMSO): 1.79 (3H), 2.88 (1H), 3.10 (1H), 4.79 (1H), 5.91 (1H), 7.24-7.60 (9H), 8.32 (3H), 12.90 (1H).

The invention claimed is:

1. An isolated (Z)-isomer of a compound according to formula (5) having no (E)-isomer present, or salt thereof, (5)

wherein R1 and R2 are, independently of each other, hydrogen or a nitrogen protecting group, and R is hydrogen or a C$_1$-C$_6$-alkyl residue.

2. The compound of formula (5) according to claim 1 wherein

R1 is hydrogen;

R2 is BOC or hydrogen; and

R is hydrogen.

3. The compound of formula (5) according to claim 2 which is (Z)—(R)-5-Biphenyl-4-yl-4-tert-butoxycarbonylamino-2-methylpent-2-enoic acid, or (Z)—(R)-4-Amino-5-biphenyl-4-yl-2-methyl-pent-2-enoic acid hydrochloride.

* * * * *